United States Patent
Wong, Jr. et al.

(10) Patent No.: US 10,598,656 B2
(45) Date of Patent: Mar. 24, 2020

(54) METHOD OF SELECTING ANALYTE TO SAMPLES USING A LATERAL FLOW DEVICE

(71) Applicant: Credo Biomedical Pte Ltd., Singapore (SG)

(72) Inventors: Winston Wong, Jr., Singapore (SG); Stephen Chang-Chi Kao, Singapore (SG)

(73) Assignee: CREDO BIOMEDICAL PTE LTD., Singapore (SG)

(*) Notice: Subject to any disclaimer, the term of this patent is extended or adjusted under 35 U.S.C. 154(b) by 610 days.

(21) Appl. No.: 14/495,266

(22) Filed: Sep. 24, 2014

(65) Prior Publication Data

US 2015/0010904 A1 Jan. 8, 2015

Related U.S. Application Data

(63) Continuation of application No. 13/618,694, filed on Sep. 14, 2012, now abandoned.
(Continued)

(51) Int. Cl.
| | | |
|---|---|---|
| G01N 33/558 | (2006.01) | |
| G01N 33/543 | (2006.01) | |
| G01N 21/80 | (2006.01) | |
| G01N 33/58 | (2006.01) | |
| G01N 21/75 | (2006.01) | |

(52) U.S. Cl.
CPC ....... G01N 33/54386 (2013.01); G01N 21/80 (2013.01); G01N 33/558 (2013.01); G01N 33/581 (2013.01); *G01N 2021/752* (2013.01); *G01N 2021/757* (2013.01); *G01N 2333/918* (2013.01); *G01N 2458/15* (2013.01)

(58) Field of Classification Search
CPC ........... G01N 33/54386; G01N 33/558; G01N 33/581; G01N 21/80; G01N 2021/752; G01N 2021/757; G01N 2333/918
See application file for complete search history.

(56) References Cited

U.S. PATENT DOCUMENTS 3,990,850 A * 11/1976 Friedman ......... G01N 33/54386
422/401
4,029,597 A 6/1977 Neisius et al.
(Continued)

FOREIGN PATENT DOCUMENTS

| CN | 200962110 A | 10/2007 |
|---|---|---|
| CN | 101769919 A | 7/2010 |

(Continued)

OTHER PUBLICATIONS

Wang et al., "Fast and long term optical sensors for pH based on sol—gels", Analytica Chimica Acta (2003) 495:45-50.*
(Continued)

*Primary Examiner* — Christopher L Chin
(74) *Attorney, Agent, or Firm* — Ladas & Parry LLP

(57) ABSTRACT

Lateral flow devices and methods of use for a molecular diagnostic assay are provided. The method is suitable for detection or monitoring of targets, including biological, chemical, and material targets that exist in very low concentrations in biological samples. The methods and devices of the present application are amenable to power source-free point of care testing.

69 Claims, 18 Drawing Sheets

Related U.S. Application Data

(60) Provisional application No. 61/535,874, filed on Sep. 16, 2011.

(56) References Cited

U.S. PATENT DOCUMENTS

| | | | | |
|---|---|---|---|---|
| 4,299,916 | A * | 11/1981 | Litman | G01N 33/52 422/534 |
| 4,461,829 | A * | 7/1984 | Greenquist | G01N 33/542 422/420 |
| 4,463,090 | A | 7/1984 | Harris | |
| 4,503,143 | A | 3/1985 | Gerber et al. | |
| 4,517,288 | A * | 5/1985 | Giegel | G01N 33/54386 435/188 |
| 4,687,732 | A * | 8/1987 | Ward | C12Q 1/00 435/14 |
| 4,754,024 | A * | 6/1988 | Schwander | C09B 62/51 534/573 |
| 4,916,056 | A | 4/1990 | Brown, III et al. | |
| 4,956,302 | A | 9/1990 | Gordon et al. | |
| 4,975,366 | A * | 12/1990 | Sudo | G01N 33/525 422/400 |
| 4,981,785 | A * | 1/1991 | Nayak | G01N 33/558 210/198.3 |
| 5,081,013 | A * | 1/1992 | Rovelli | G01N 33/54386 422/417 |
| 5,279,937 | A * | 1/1994 | Rowe | C12Q 1/6816 435/23 |
| 5,374,524 | A | 12/1994 | Miller | |
| 5,403,744 | A | 4/1995 | Zimmerle | |
| 5,409,664 | A | 4/1995 | Allen | |
| 5,591,645 | A | 1/1997 | Rosenstein | |
| 5,622,871 | A | 4/1997 | May et al. | |
| 5,641,639 | A * | 6/1997 | Perry | G01N 33/54386 422/408 |
| 5,654,162 | A | 8/1997 | Guire et al. | |
| 5,710,005 | A | 1/1998 | Rittenburg | |
| 5,714,389 | A | 2/1998 | Charlton et al. | |
| 5,989,921 | A | 11/1999 | Charlton et al. | |
| 6,020,147 | A | 2/2000 | Guire et al. | |
| 6,251,621 | B1 | 6/2001 | Lawrence et al. | |
| 6,306,642 | B1 | 10/2001 | Nelson et al. | |
| 6,348,319 | B1 | 2/2002 | Braach-Maksvytis et al. | |
| 6,485,982 | B1 | 11/2002 | Charlton | |
| 6,534,320 | B2 | 3/2003 | Ching et al. | |
| 6,565,808 | B2 | 5/2003 | Hudak et al. | |
| 6,682,903 | B2 * | 1/2004 | Saunders | G01N 33/542 435/18 |
| 6,706,539 | B2 | 3/2004 | Nelson et al. | |
| 6,759,190 | B2 | 7/2004 | Lin et al. | |
| 6,767,714 | B2 | 7/2004 | Nazareth et al. | |
| 7,132,078 | B2 | 11/2006 | Rawson et al. | |
| 7,300,802 | B2 | 11/2007 | Paek et al. | |
| 7,504,235 | B2 | 3/2009 | Song | |
| 7,575,887 | B2 | 8/2009 | Song | |
| 7,591,978 | B2 | 9/2009 | Dwir et al. | |
| 7,632,687 | B2 | 12/2009 | Gokhan | |
| 7,691,644 | B2 | 4/2010 | Lambotte et al. | |
| 7,709,272 | B2 | 5/2010 | Fuks et al. | |
| 7,816,122 | B2 | 10/2010 | Clark et al. | |
| 7,935,538 | B2 | 5/2011 | Song et al. | |
| 8,377,643 | B2 | 2/2013 | Mehra et al. | |
| 9,618,506 | B2 * | 4/2017 | Lowe | B01L 3/5027 |
| 2001/0019821 | A1 | 9/2001 | Smith | |
| 2004/0048274 | A1 | 3/2004 | Breindahl | |
| 2004/0110167 | A1 * | 6/2004 | Gerdes | C12Q 1/6834 435/6.11 |
| 2004/0152207 | A1 | 8/2004 | Nelson et al. | |
| 2004/0214253 | A1 | 10/2004 | Paek et al. | |
| 2006/0057661 | A1 * | 3/2006 | Song | C12Q 1/04 435/25 |
| 2007/0122873 | A1 * | 5/2007 | Colpas | C12Q 1/04 435/34 |
| 2011/0039290 | A1 * | 2/2011 | Clausen | C12Q 1/32 435/26 |
| 2011/0053181 | A1 * | 3/2011 | Hazama | G01N 33/558 435/7.9 |
| 2011/0086359 | A1 | 4/2011 | Babu et al. | |

FOREIGN PATENT DOCUMENTS

| | | |
|---|---|---|
| EP | 0175560 A2 | 3/1986 |
| EP | 0762123 A1 | 3/1997 |
| WO | 8808536 A1 | 11/1988 |
| WO | 9401775 A1 | 1/1994 |
| WO | 0031538 A1 | 6/2000 |
| WO | 2004092342 A2 | 10/2004 |
| WO | 2007082544 A1 | 7/2007 |
| WO | 2008051196 A2 | 5/2008 |
| WO | 2009024805 A1 | 2/2009 |

OTHER PUBLICATIONS

Duan et al., "Rapid and simultaneous detection of human hepatitis B virus and hepatitis C virus antibodies based on a protein chip assay using nano-gold immunological amplification and silver staining method," BMC Infectious Diseases, Jul. 6, 2005, vol. 5, No. 53, p. 2 of 8.

Richter et al., "Review on Hydrogel-based pH Sensors and Microsensors," Sensors, Jan. 25, 2008, vol. 8, pp. 561-581.

Schwartz, Smart Materials, 2009, Section 24.3.2.1.

Branched DNA Assay, May 5, 2011, http://web.archive.org/web/20110505022017/http://en.wikipedia.org/wiki/branched_DNA_assay.

The Chinese Office Actions, dated Apr. 3, 2015 and Nov. 19, 2015, in the related Chinese Patent Application No. 201280041999.3.

The European Office Actions, dated Nov. 2, 2015 and Mar. 24, 2016, in the related European Patent Application No. 12831147.9.

The extended European Search Report, dated Feb. 13, 2015, in the related European Patent Application No. 12831147.9.

The Israel Office Action, dated Mar. 5, 2015, in the related Israel Patent Application No. 231514.

The Japanese Office Actions, dated Jun. 16, 2015 and Nov. 4, 2015, in the related Japanese Patent Application No. 2014-530884.

The Singapore Search Report and Written Opinions, dated Mar. 18, 2015 and Oct. 14, 2015, in the related Singapore Patent Application No. 11201400677P.

Microbe Wiki, Bacillus Stearothermophilus NEUF2011, article, website: http://microbewiki.kenyon.edu/index.php/Bacillus_stearothermophilus_NEUF2011, Nov. 1, 2011.

The International Search Report and Written Opinion, dated Mar. 15, 2013, in the related PCT Application No. PCT/US2012/055542.

The US Office Actions, dated Feb. 16, 2016, Dec. 5, 2016 and Mar. 23, 2017, in related U.S. Appl. No. 14/337,805.

The US Office Actions, dated Apr. 21, 2017, in related U.S. Appl. No. 14/345,276.

* cited by examiner

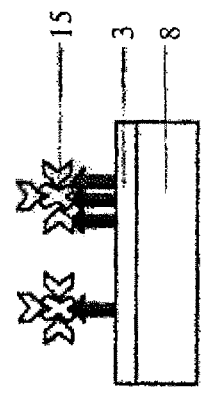
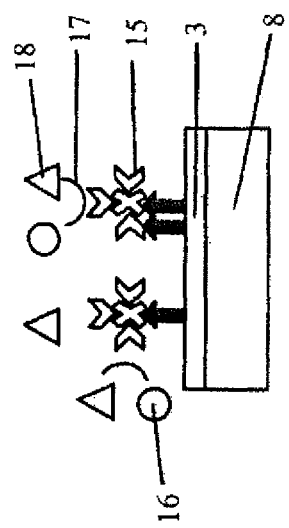
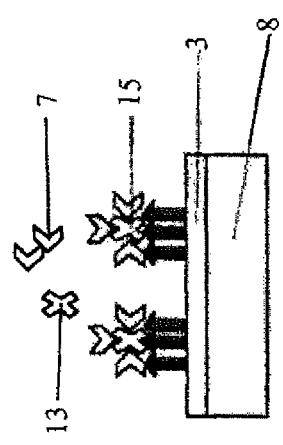
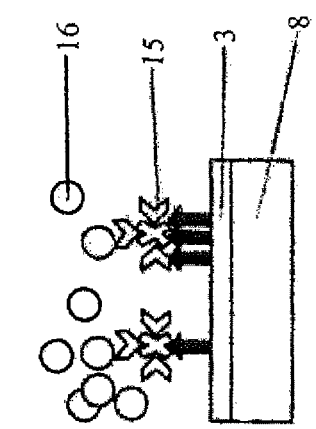

METHOD OF SELECTING ANALYTE TO SAMPLES USING A LATERAL FLOW DEVICE

CROSS-REFERENCE TO RELATED APPLICATIONS

This application is a Continuation of application Ser. No. 13/618,694, filed Sep. 14, 2012, which claims priority Provisional Patent Application Ser. No. 61/535,874, filed Sep. 16, 2011. The priority of each prior mentioned application is claimed. Each of prior mentioned applications is hereby incorporated by reference herein in its entirety.

FIELD OF THE INVENTION

The invention relates to the general field of molecular biology, molecular diagnostics, nucleic acid testing (NAT), medical science and biotechnology. The invention is suitable for detection or monitoring traces of chemical and/or biological target(s) that exist(s) in a very low concentration in samples, including, not exclusively, biological samples, materials, organic or inorganic samples. The traces of chemical and/or biological target(s) can include biological/chemical products, fragments or whole target(s), e.g. nucleic acid sequences, cells, viruses, pathogens, chemicals, with applications in point of care/site/interest and laboratory in fields such as pharmacogenomics, pathogen detection and monitoring, determination of genetic predisposition, genetic classification for clinical trials, diagnostics, prognostics, infectious disease diagnostics and monitoring, bio-defense, forensic analysis, paternity testing, animal and plant breeding, food testing, human identification, genetically modified organism testing, chemical contamination, food safety, monitoring and tracking in production chain, and production in-line monitoring/control.

BACKGROUND

Molecular diagnostics has been a routine clinical laboratory procedure for biological detection and monitoring. A specimen of a biological sample coming from various biological sources usually contains a mixture of chemicals, metabolites, macromolecules, cells, virions, organisms, and nucleic acid sequences. Typically, two common challenges exist for detection and monitoring: background interference and limits of detection (LOD). Namely, the target biological samples are usually present in a very small amount compared with other background components in the biological sample. Such non-target background components may interfere with the detection downstream. LOD becomes an issue when not enough copies of the target exist in the sample. The same LOD challenge is the same as in chemical analysis, which usually requires highly sophisticated instruments for conducting analysis work. Examples include using mass spectrometry for detection of bis(n-butyl)phthalate plasticizer contamination in the food supply chain, melamine contamination in milk, cadmium and heavy metal contamination in the soil or food. The background interference is an order of magnitude higher than the contaminants. On-site analysis is usually difficult without extensive treatment in the laboratory involving instruments such as a GC spectrometer or mass spectrometer, for example.

Background interference is usually solved by purifying the sample during the preparation stage. Targets are captured and background components are removed by one or more washing procedure(s). Typical examples include: Enzyme-linked Immunosorbent Assay (ELISA) and different chromatographic methods. Lateral flow platforms can also be used to capture targets while background components are removed from the immobilized targets. Another example of a purification procedure for nucleic acid targets are purification kits such as the Qiagen QIAamp DSP DNA Blood Mini Kit.

The LOD issue for nucleic acids is usually resolved by amplification of the sample target first, which allows later detection by fluorescence emission, electrical and electronic methods, e.g. voltametry, current measurement, capacitance measurement, or impedance spectroscopy. Among these detection or amplification methods, electrical power is required to provide the light or conduct the electrical/electronic detection. One example of resolving the LOD issue with low abundance nucleic acid targets is by amplifying nucleic acid targets in vitro by using the polymerase-chain reaction (PCR). The signal associated with the presence of the target sequence can be further amplified by fluorescence methods. Each PCR amplicon that is labeled by fluorescent tags(s) can produce 1000 or 10,000 more protons in a single excitation/measurement period when a fluorescence beacon or probe is used to detect the amplicon. Another example is a *Campylobacter*-like organism test, in which *H. pylori* cells multiplies in the culture and is thus amplified, and where urease secreted from the amplified cells can be detected after the number of cells passes the detection threshold. Yet another example is the screening of MRSA. This detection method differentiates the colonies of the multiplied and amplified cells on a culture medium.

However, current methods which rely on removal of various combinations of background interference and amplification detection have not filled the need for a robust, cost effective, rapid, easy to use detection method for targets, which is compatible in resource limited environments. The requirement for an electrical power source to perform the current tests by powering the instrument or providing the temperature incubation has restricted access to this technology in resource-poor regions or conditions. The time required to practice the current methods is long. Many hours or days are required to produce enough biological targets to generate sufficient detection signals. The amplification step used for pathogen detection, metabolite determination, or nucleic acid sequence detection usually requires expensive laboratory instruments and trained specialists to run the instruments. In the case of PCR, care is required to handle labile reagents, and special diligence is essential to avoid contamination between samples. Moreover, the instruments required to perform PCR are expensive and complex. The above considerations are severe limitations that prevent POC (point of care) use or provide rapid sample-to-result in less than 30 minutes. The present invention provides solutions to these and other needs.

SUMMARY

Methods and devices for molecular detection or diagnostic assays are provided by the present invention. The methods disclosed herein are suitable for detection or monitoring of one or more targets that exist in very low concentrations in samples including biological, chemical and material but not exclusively limited to these, and generally allow detection in the absence of the replication of the target or amplification of a fragment or part of the target. The methods and devices of the present application are amenable to point of care detection without the requirement for access to electrical power.

In one aspect, the present invention provides a method for detecting an analyte by performing the steps of i) providing a lateral flow assay device that comprises a chromatographic medium that includes: (a) a sample loading zone located upstream of a detection zone; (b) a reporting carrier zone located between the sample loading zone and a detection zone, wherein said reporting carrier zone comprises a reporting carrier capable of forming a complex with the analyte said reporting carrier comprising a carrier and one or more proficient enzyme cassettes; and (c) a detection zone, wherein the detection zone comprises a capture component for the analyte and an indicator; ii) Contacting the sample application zone with the test sample, wherein the test sample travels through the reporting carrier zone along the chromatographic medium from the sample loading zone to the detection zone and beyond the detection zone; iii) adding a substrate to the detection zone wherein the substrate undergoes a reaction in the presence of proficient enzyme analyte containing reporting carrier; and iv) generating a response of the indicator within the detection zone that corresponds to the presence or absence of the analyte in the test sample.

In another aspect, the present invention provides a device for detecting an analyte by comprising: a chromatographic medium that includes: a sample loading zone located upstream of a detection zone; a reporting carrier zone located between the sample loading zone and a detection zone, wherein said reporting carrier zone comprises a reporting carrier capable of forming a complex with the analyte said reporting carrier comprising a carrier and one or more proficient enzyme cassettes; and a detection zone, wherein the detection zone comprises a capture component for the analyte and an indicator wherein the indicator detects a reaction of a substrate in the presence of a proficient enzyme thereby detecting the product of the analyte enzyme reporting carrier complex and a substrate is detected, thereby detecting the presence of the analyte.

In one aspect, the present invention provides a kit for detecting an analyte comprising a lateral flow assay device comprising: a porous membrane comprising: a sample loading zone; a reporting carrier zone down stream of the loading zone, wherein said reporting carrier zone comprises a reporting carrier capable of forming a complex with the analyte; a detection zone down stream of the reporting carrier zone, wherein the detection zone comprises a capture component and an indicator; and a substrate for the proficient enzyme; wherein the substrate is applied to the detection zone after the test sample has been allowed to flow through the lateral flow device and the product of the enzyme and substrate is detected.

In some embodiments, it is also possible to implement the method comprising these steps, but not in the order listed above. For example, it is possible to (a) immobilize the analyte from a sample suspected of containing the analyte (b) contacting the immobilized analyte to a reporting carrier to form a reporting carrier-analyte complex, where the reporting complex comprises a proficient enzyme, (c) providing a substrate for the proficient enzyme, and (d) detecting fluctuation as a result of proficient enzyme assisted reactions, for example, product of the reaction, thereby detecting the presence of the analyte.

In various embodiments of this aspect, the analyte is a protein, nucleic acid cell, part of a cell or pathogen, pathogen, virion, component of cellular or extracellular matrix, or small molecules. In various embodiments of this aspect, the reporter carrier contains an antibody or nucleic acid.

In certain embodiments of this aspect, the proficient enzyme can be urease, phosphocholine phosphatase, beta-galactosidase, xylose reductase, shikimate dehydrogenase, malate dehydrogenase, neopullulanase, subtilisin, 4-phytase, acetylcholinesterase, laccase, bacterial leucyl aminopeptidase, tripeptidyl-peptidase I, coagulation factor VIIa, trypsin, betafructofuranosidase.

In an embodiment of this aspect, the antibody is associated with the proficient enzyme by noncovalent interactions. Alternatively, the antibody or nucleic acid is covalently attached to the proficient enzyme.

In an additional embodiment of this aspect, the method further uses one or more inactive pro-enzymes. A pro-enzyme is any of a group of compounds that are inactive precursors of enzymes and require some change (such as the hydrolysis of a fragment that masks an active enzyme) to become active.

In another embodiment of this aspect, the detection of the product of the proficient enzyme is by detection of a pH change, which may be determined using a pH sensitive hydrogel that can have gold nanoparticles that change color in response to pH changes.

In a further embodiment of this aspect, the detection of the product of the proficient enzyme is by colorimetric change, where the colorimetric change is due to fluctuations as a result of proficient enzyme assisted reaction, for example, protonation or deprotonation of the dye material or silver ion reduction.

In yet further embodiments of this aspect, the detection of the product of the proficient enzyme is by precipitation as the result of the effect of the proficient enzyme-assisted reaction, for example, precipitation of a soluble component, which can be a protein including BSA or pH sensitive polymer, which forms aggregates with changes in pH. The change of pH results in the shift of the surface charge of the polymer. As a consequence of the surface charge variation, the 3-D structure of the polymer molecules changes and the hydrophobic part of the polymer is exposed. The exposure of the hydrophobic region of the polymer increases the entropy. These hydrophobic parts of the polymer would fonn non-covalent interactions thus forming aggregates. Examples of pH sensitive polymers include: methyl acrylic acid, methyl methacrylate, methacrylic acid 2-(dimethylamino) ethyl ester, and N-hydroxymethyl acrylamide.

In another aspect, the present invention provides a molecular diagnostic device that has (a) a sample loading zone, (b) a reporting carrier zone, where the reporting carrier zone contains a reporting carrier and a proficient enzyme, (c) a source of substrate for the proficient enzyme; and (d) a detection zone, where the detection zone contains a capture component.

In some embodiments of this aspect, the device also has a positive control zone.

In some embodiments of this aspect, the sample loading zone is a sample loading pad.

In some embodiments of this aspect, the reporting carrier zone is a conjugate pad.

In some embodiments of this aspect, the detection area comprises a porous membrane.

In some embodiments of this aspect, the device has a rigid or flexible backing material.

In various embodiments of this aspect, the reporter carrier contains an antibody or nucleic acid.

In certain embodiments of this aspect, the proficient enzyme can be urease, phosphocholine phosphatase, beta-galactosidase, xylose reductase, shikimate dehydrogenase, malate dehydrogenase, neopullulanase, carboxylesterase, subtilisin, 4-phytase, acetylcholinesterase, laccase, bacterial leucyl aminopeptidase, tripeptidyl-peptidase I, coagulation factor VIIa, trypsin, betafructofuranosidase. In certain embodiments of the present invention when a pro-enzyme it utilized, the pro-enzyme may be a pro-enzyme selected from the group of pro-enzymes of the above proficient enzymes.

In an embodiment of this aspect, the antibody is associated with the proficient enzyme by noncovalent interactions. Alternatively, the antibody or nucleic acid is covalently attached to the proficient enzyme.

In an additional embodiment of this aspect, the method further uses one or more inactive pro-enzymes.

In another embodiment of this aspect, the detection of the product of the proficient enzyme is by detection of a pH change, which may be determined using a pH sensitive hydrogel that can have gold nanoparticles that change color in response to pH changes.

In a further embodiment of this aspect, the detection of the product of the proficient enzyme is by colorimetric change, where the colorimetric change is due to the effect of a proficient enzyme assisted reaction, for example, protonation or deportonation of the dye material or silver ion reduction.

In yet further embodiments of this aspect, the detection of the product of the proficient enzyme is by precipitation as the result of the fluctuation of the proficient enzyme-assisted reaction, for example, precipitation of a soluble component, which can be a protein including BSA or pH sensitive polymer. Examples of pH sensitive polymers include: methyl acrylic acid, methyl methacrylate, methacrylic acid 2-(dimethylamino) ethyl ester, and N-hydroxymethyl acrylamide.

In another further aspect, the present invention provides a molecular diagnostic device that has (a) a sample loading zone, (b) a pre-reporting carrier zone, if there is one, where the pre-reporting carrier zone contains a reporting carrier and a proficient enzyme, (c) a source of substrate for the proficient enzyme and a reporting carrier for the pre-reporting carrier; and (d) a detection zone, where the detection zone contains a capture component.

In another further aspect, the present invention provides a molecular diagnostic device that has a detection zone, where the detection zone contains a capture component. The pre-reporting carrier, reporting carrier, or substrate could be added to the detection sequentially.

In another further aspect, the present invention provides a molecular diagnostic device that has a detection zone, where the detection zone contains a capture component. The detection zone could be placed and moved amongst multiple reagent containers that contain one or more of the following: pre-reporting carrier, reporting carrier, and substrate.

In yet another further aspect, the present invention provides a molecular diagnostic device that utilizes combinations of the process highlighted in the foregoing paragraphs.

DETAILED DESCRIPTION

Figure 1:
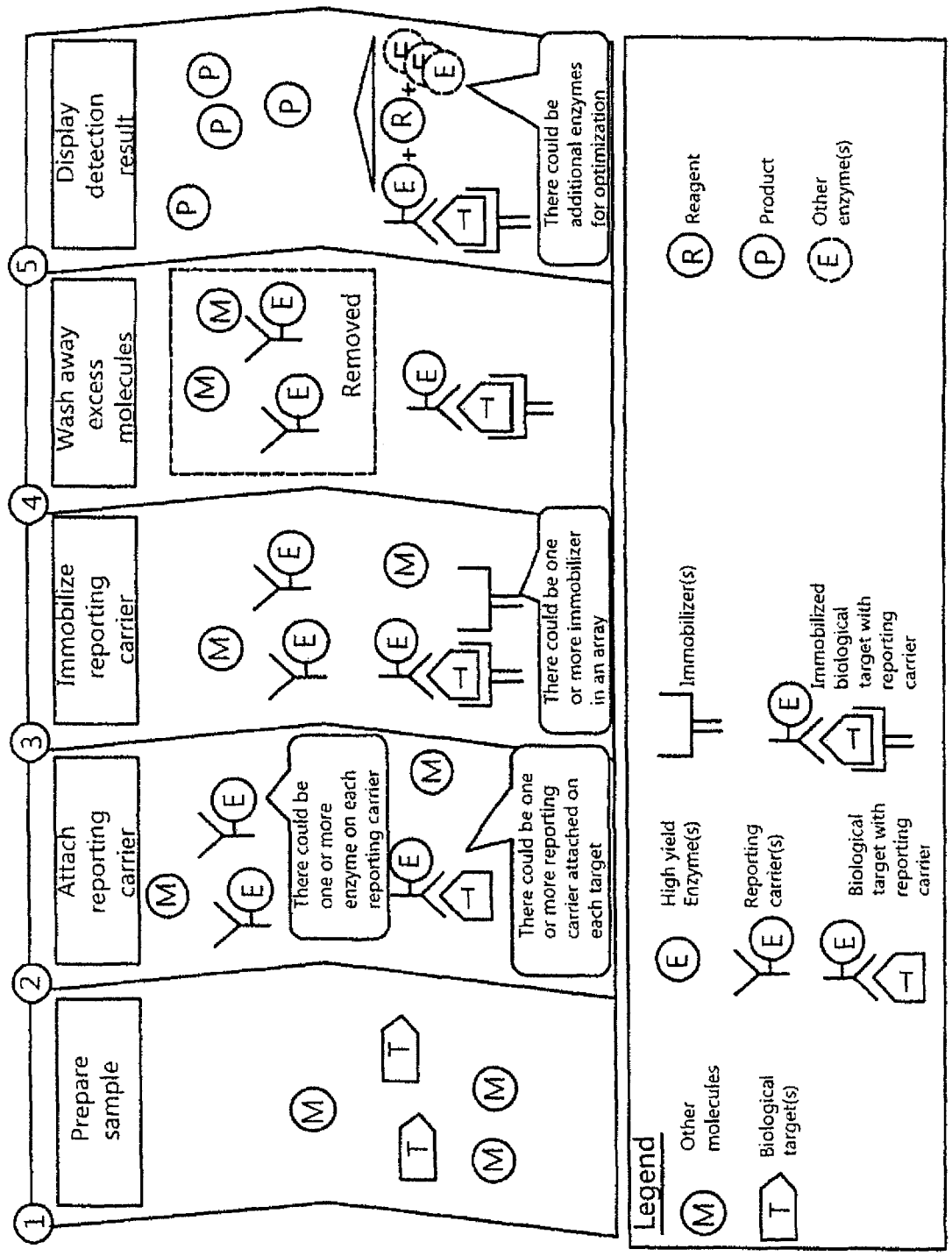
FIG. 1 shows general steps for target detection, including sample preparation, signal carrier attachment, signal carrier immobilization, excess molecule removal, and result display.

The present invention generally provides methods and devices for the detection of analytes and targets in a sample with a sufficiently low limit of detection (LOD) to reduce or eliminate the need for an amplification step prior to detection. The methods disclosed herein provide a significantly less complex process with a reduced requirement for sample purity. The methods and devices of the present invention also provide a streamlined sample preparation process, including for sample enrichment, purification, labeling, and detection.

A lateral flow molecular diagnostic device for detecting the presence of an analyte in a test sample comprising a chromatographic medium that includes: (a) a sample loading zone located upstream of a detection zone; (b) a reporting carrier zone located between the sample loading zone and a detection zone, wherein said reporting carrier zone comprises a reporting carrier capable of forming a complex with the analyte; (c) a substrate for the proficient enzyme; and (d) a detection zone, wherein the detection zone comprises a capture component for the analyte and a substrate for the proficient enzyme; wherein the product of the enzyme and substrate is detected.

The lateral flow diagnostic device for detecting the presence of an analyte in a test sample may further comprise a positive control zone downstream of the detection zone.

Attempts at development of nucleic acid detection devices for use in the near-bedside environment have been made. Some products have partially filled this need by bringing the test outside the clinical laboratory. However, these approaches do not (1) eliminate the reliance on an amplification step and associated equipment, (2) reduce the storage requirement for detection materials, (3) eliminate the reliance on a complex analyzer that reads an optical signal from the amplification; or (4) eliminate the reliance on an electrical power supply. The amplified nucleic acid fragment as the result of the said nucleic acid amplification test has fundamentally increased the risk of cross-contamination between samples.

Lateral flow devices that seek to replace the need for a scanner or analyzer have also be described in, for example, US 2011086359, WO2004092342, Anal. Chem, 2004, V76, P888, and Anal. Chem. 2009, V81, P1660. However, these methods, while not requiring a complex analyzer, suffer from a lack of sensitivity for direct detection without pre-amplification. For example, pathogen nucleic acid detection generally requires 1,000 copies or better to achieve sufficient sensitivity; other reports describe a requirement for a minimum of 100,000,000 copies of amplified targets for detection. These methods have a requirement for amplification instruments and reagents, which are sensitive to storage condition; require specialists to perform the amplification of the target nucleic acids; and are sensitive to cross contamination through the repeated use of the same amplification instruments.

There are also rapid kits for detecting presence of a pathogen, such as CLO (http://www.medicinenet.com/helicobacter_pylori/article.htm#2diagnosis), but these methods require (1) long incubation time (from a few hours to days)

to multiply biological targets; (2) specialists to take a biopsy; and (3) specialist to interpret the result.

As described in detail herein, the present invention provides methods and devices to detect one or more targets, including biological, chemical, or material targets with minimal or no amplification prior to the detection. In part, this is accomplished through the use of stable and robust proficient enzyme systems that allow direct detection of a biological target without pre-amplification. In the case of nucleic acid detection, there is reduced risk of cross contamination because the target is not replicated and the entire device is disposable. Detection time is much reduced, with sample-to-result times of less than 1 hour or as short as 15 minutes. The enzymes used in the present invention are preferably stable at room temperature. In some embodiments, the invention enables detection without sophisticated instrumentation, thus making the invention amenable to point of care (POC) applications.

Accordingly, the methods and devices of the present invention provide for significantly reduced setup costs and equipment requirements for point of care detection and are amenable for application to a disposable kit. These features allow for embodiments which can be operated directly by consumers or other personnel without prior training before use. Furthermore, the methods and devices of the present invention can be integrated into existing workflows to improve limit of detection (LOD) and/or detection time.

DEFINITIONS

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

An "analyte" or "target" refers to a compound to be detected. Such compounds can include cells, parts of cells or pathogens, pathogens, virions, components of cellular or extracellular matrix, small molecules, peptides, proteins, nucleic acids, as well as other chemical entities.

Chromatographic medium may be made from any of a variety of materials through which the test sample is capable of passing. For example, the chromatographic medium may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

Figure 3:
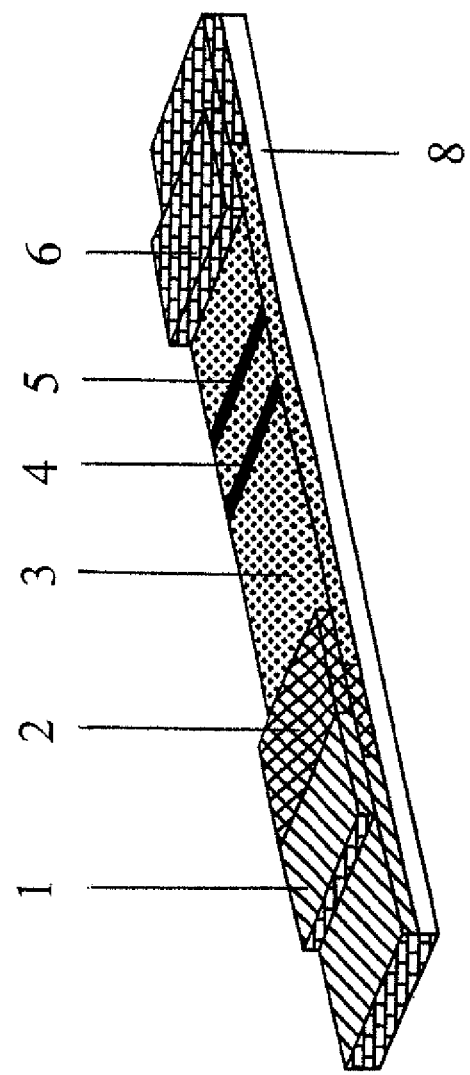
FIG. 3 shows implementation on a lateral flow device.
Figure 4B:
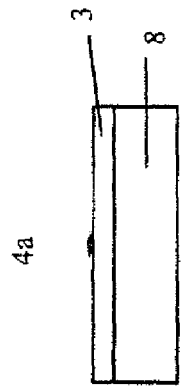
FIG. 4A-4H shows various embodiments of a lateral flow device.
Figure 4D:
Figure 4A:
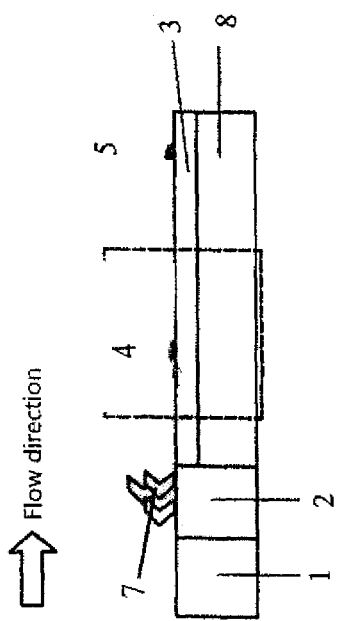
Figure 4C:
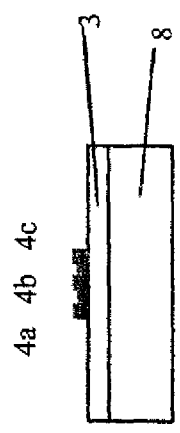
Figure 4F:
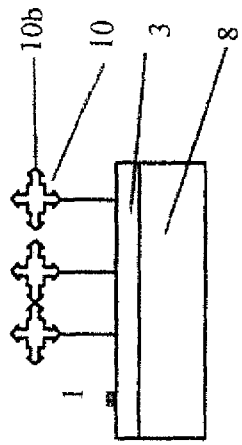
Figure 4H:
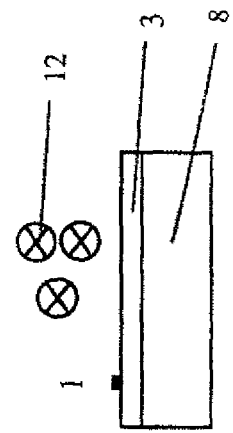
Figure 4E:
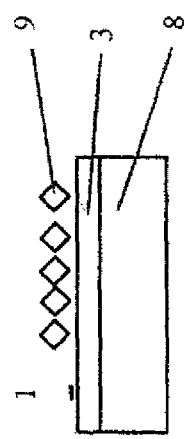
Figure 4G:
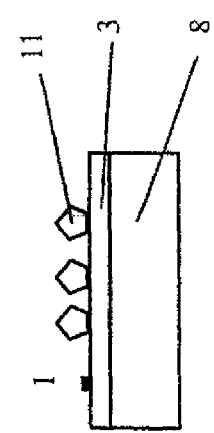
Figure 5A:
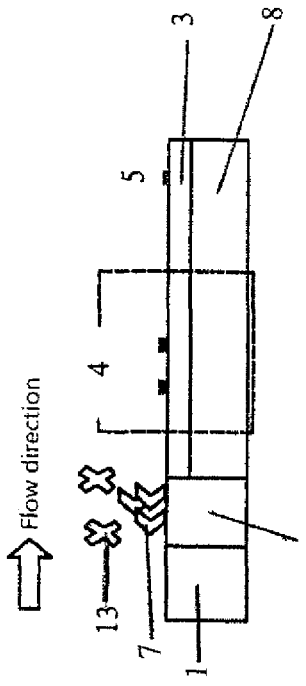
FIG. 5 A-5L shows various embodiments of the function of a lateral flow device.
Figure 5B:
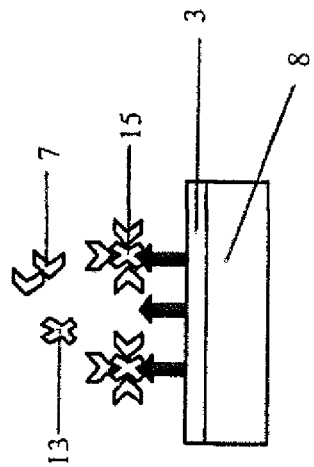
Figure 5C:
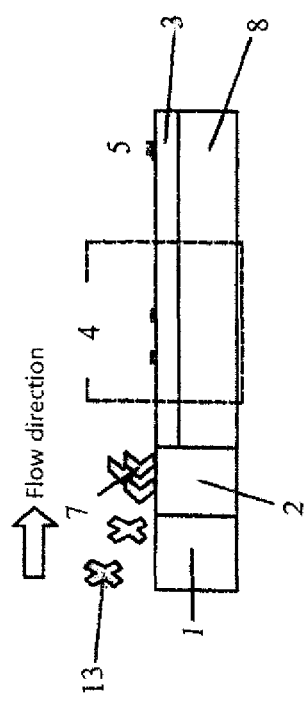
Figure 5D:
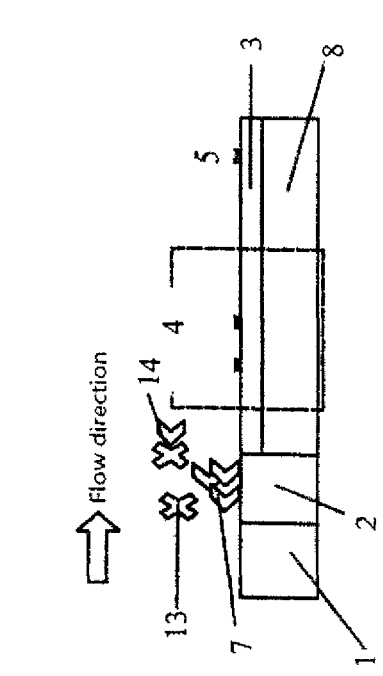
Figure 5I:
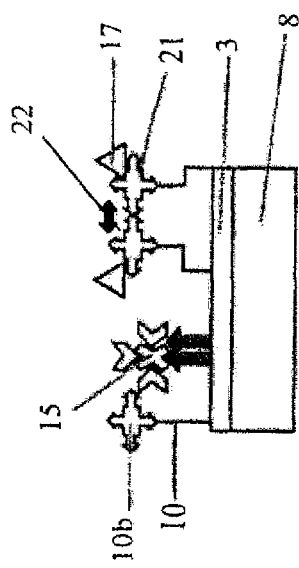
Figure 5J:
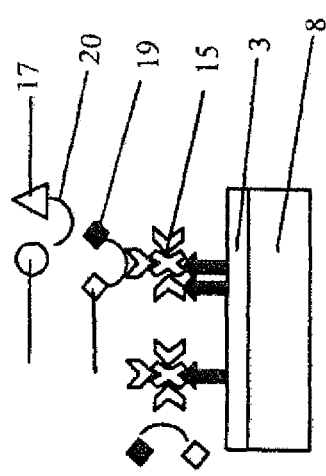
Figure 5K:
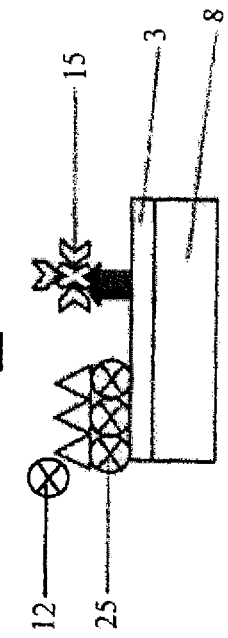
Figure 5L:
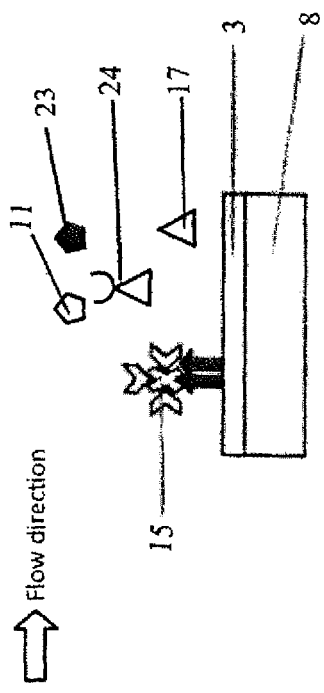

As stated above, the support material carries the chromatographic medium. For example, the support 21 may be positioned directly adjacent to the chromatographic medium as shown in FIG. 3, or one or more intervening layers may be positioned between the chromatographic medium and the support material. Regardless, the support material may generally be formed from any material able to carry the chromatographic medium. The support material may be formed from a material that is transmissive to light, such as transparent or optically diffuse (e.g., translucent) materials. Also, it is generally desired that the support material is liquid-impermeable so that fluid flowing through the medium does not leak through the support material. Examples of suitable materials for the support include, but are not limited to, glass; polymeric materials, such as polystyrene, polypropylene, polyester (e.g., Mylar RTM film), polybutadiene, polyvinylchloride, polyamide, polycarbonate, epoxides, methacrylates, and polymelamine; and so forth. To provide a sufficient structural backing for the chromatographic medium, the support material is generally selected to have a certain minimum thickness. Likewise, the thickness of the support 8 is typically not so large as to adversely affect its optical properties. Thus, for example, the support material may have a thickness that ranges from about 100 to about 5,000 micrometers, in some embodiments from about 150 to about 2,000 micrometers, and in some embodiments, from about 250 to about 1,000 micrometers.

As is well known the art, the chromatographic medium may be cast onto the support material wherein the resulting laminate may be die-cut to the desired size and shape. Alternatively, the chromatographic medium may simply be laminated to the support material with, for example, an adhesive. In some embodiments, a nitrocellulose or nylon porous membrane is adhered to a film.

The lateral flow device also contains an absorbent material that is positioned adjacent to the chromatographic medium at the distal end, That is the end of the chromatographic medium farthest from the sample loading zone. The absorbent material assists in promoting capillary action and fluid flow through the chromatographic medium. In addition, the absorbent material receives fluid that has migrated through the entire chromatographic medium and thus draws any unreacted components away from the detection and control regions to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

The sample loading zone may be formed by a separate material, such as a pad. Some suitable materials that may be used to form such sample pads include, but are not limited to, nitrocellulose, cellulose, porous polyethylene pads, and glass fiber filter paper. If desired, the sample loading zone may also contain one or more pretreatment reagents, either diffusively or non-diffusively attached thereto. In the illustrated embodiment, the test sample travels from the sample loading zone to a reporting carrier zone that is in communication with the sample loading zone. The reporting carrier zone may be formed on the chromatographic medium. Alternatively, as shown in FIG. 3, the reporting carrier zone is formed from a separate material or pad. Such a reagent pad may be formed from any material through which the test sample is capable of passing, such as glass fibers.

An "indicator" refers to any of various substances, such as litmus, phenolphthalein, or bromothymol blue, Potassium I-hydroxy-4-[1-(2-hydroxyethylsulphonyl)phenylazo]-naphthalene-2-sulphonate, cellulose acetate coupled potassium I-hydroxy-4-[1-(2-hydroxyethylsulphonyl)phenylazo]-naphthalene-2-sulphonate and the like that indicate the presence, absence, or concentration of another substance or the degree of reaction between two or more substances by means of a characteristic change, especially in color.

A "sample" refers to any source which is suspected of containing an analyte or target molecule. Examples of samples which may be tested using the present invention include, but are not limited to, blood, serum, plasma, urine, saliva, cerebrospinal fluid, lymph fluids, tissue and tissue and cell extracts, cell culture supernatants, biopsy specimens, paraffin embedded tissue, soil, fruit, juice, oil, milk, food, water, among others. A sample can be suspended or dissolved in liquid materials such as buffers, extractants, solvents, and the like.

"Reporting carrier" refers to an entity which binds and forms a complex with a target or analyte and reports the presence of the target or analyte. The reporting carrier can comprise a protein or nucleic acid or another moiety that is able to form a complex with an analyte or target molecule. The reporting carrier is associated with a proficient enzyme cassette, which can comprise combinations of enzymes and substrates, which are only active in the presence of a target or analyte. The enzyme cassette contains at least one proficient enzyme that is conjugated to a reporting carrier.

In some embodiments, the carrier is an antibody or oligonucleotide.

"Proficient enzyme" or "high yield enzyme" refers to an enzyme that can generate a product at a high rate that approaches the diffusion limit.

"Capture component" refers generally to a molecule that specifically recognizes and complexes with a target or analyte without preventing a reporting carrier from forming a complex with the same target or analyte. Generally, the capture component is immobilized to a matrix on the chromatographic membrane.

"Pre-reporting carrier" refers generally to a molecule that specifically binds to the analyte before the association of reporting carrier. A pre-reporting carrier generally does not contain a proficient enzyme.

A "proficient enzyme conjugate" refers generally to a proficient enzyme, which is conjugated to a reporting carrier. The nature of the interaction is covalent or non-covalent or a hybrid of both.

Components And Methods
Reporting Carrier
A. Carriers

A reporting carrier typically comprises two components: the first component is a carrier which is able to form a specific complex with a target or analyte, which can be biological, chemical or other types. The other component is one or more proficient enzyme cassettes. Among the carriers that can be used in the practice of the present invention include, but are not limited to, nucleic acids with a sequence which is complementary to at least part of a target nucleic acid sequence, antibodies, aptamers, solid or porous microparticles, and synthetic polymer with an imprinted structure that is complimentary to at least part of the target. Solid, shell-core, or porous microparticles can be part of the carrier, which can improve the control of the flow to direct the carrier to the reaction pads. This can be achieved by changing the size or density of the carrier or providing the utility of magnet-driven particle movement, if particles can be polarized magnetically, e.g. paramagnetic particles.

In another embodiment, a pre-reporting carrier, which does not contain a proficient enzyme, forms a pre-reporting carrier-analyte complex, said complex A. Complex A can be captured and immobilized by an immobilizer. The pre-reporting carrier alone does not bind with the immobilizer. Without the presence of the analyte, there is no complex formation and the pre-reporting carrier is washed away.

The reporting carrier is specific to the analyte. A pre-reporting carrier could be used to form a complex with the analyte. Such association is possible when all three components are present in the solution. In a preferred embodiment, a pre-reporting carrier is added to the sample solution prior to the sample solution being applied to the lateral flow assay device. The analyte pre-reporting carrier complex comes into contact in the reporter carrier zone, wherein the reporting carrier forms an association with the complex. The analyte is captured and immobilised by the surface capture agent in the detection zone. The association of the analyte and the pre-reporting carrier does not inhibit the immobilisation of the analyte. In the presence of the analyte and pre-reporting carrier, the complex of the said two component would be immobilised via the interaction of the analyte and the surface capture agent in the detection zone. The reporting carrier is then allowed to be immobilised when it associated with the complex. In the absence of analyte or pre-reporting carrier analyte complex, the reporting carrier would not be able to be immobilised and would move past the detection zone as the solvent moves and optional washes move down the lateral flow device.

The purpose of the pre-reporting carrier is multiple. One is to increase specificity to the target analyte. The conjugation of the enzyme to the reporting carrier could restrict the ability to maximize the binding selectivity to the target analyte over background non-targets. In the case of nucleic acid, the steric hindrance or coulomb charge effect from the conjugated enzyme could affect he selectivity of the hybridization. The other purpose is to increase the signal amplification process through cascade binding. One example is the detection of a small analyte. When the molecular size of the analyte is too small, it is difficult to have more than one reporting carrier forming complex with one analyte. There is more surface area per analyte molecule after it forms a complex, said complex A, with the pre-reporting carrier. Larger surface area and functional groups are created as a result of complex A formation. The added surface area and functional groups would allow more than one reporting carrier to be associated with the complex, which comprise one analyte. More reporting carriers would produce more signals and therefore, further improve the signal to noise ratio. Using a pre-reporting carrier increases the target surface area to allow more reporting carriers specific binding events per analyte to take place.

Another embodiment reduces the complexity of the reporting carrier design and increases multiplicity to the target analytes, e.g. virus gene polymorphism or multiple nucleic acid sequence targets. A mixture of the various pre-reporting carriers could be designed to react with each specific genotype or sequence. All the pre-reporting carriers could contain one or more tags that is/are specific to the reporting carrier. When using the same single tag, the reporting carrier binds to the tag specifically but without differentiation between the pre-reporting carriers. When using different tags, it is useful to group several targets separately if a different reporting carrier is designed to each tag.

Figure 6A:
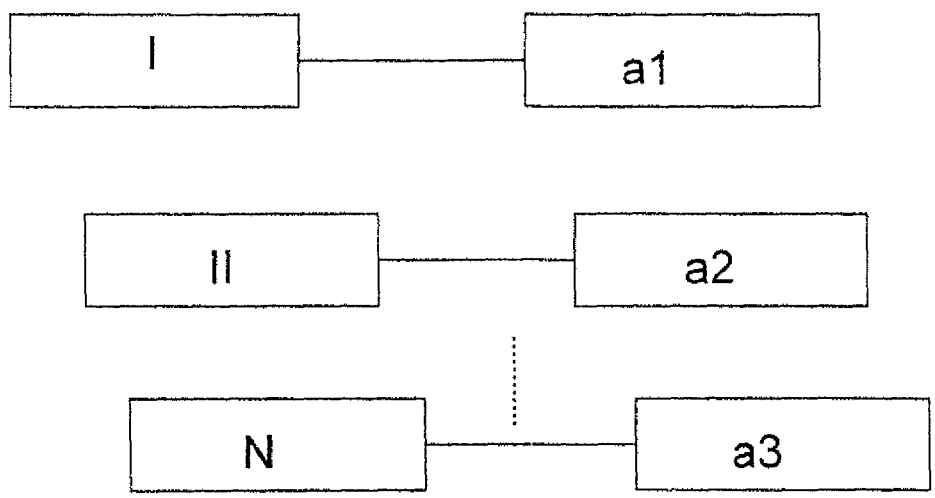
FIG. 6A-6H shows different embodiments of pre-reporter carriers for the detection of nucleic acid targets.
Figure 6B:
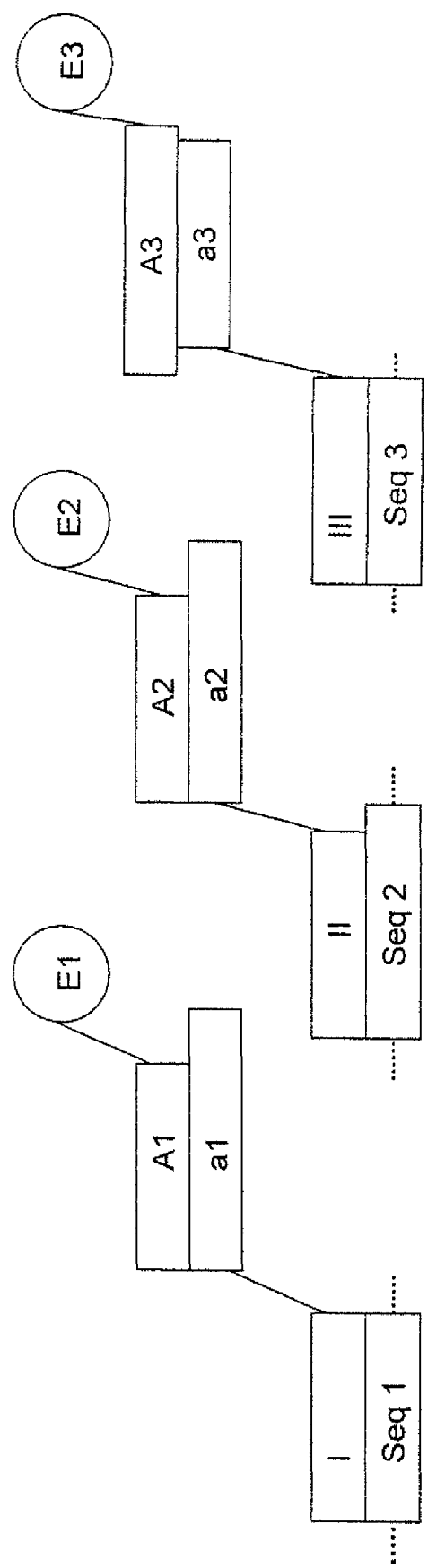
Figure 6C:
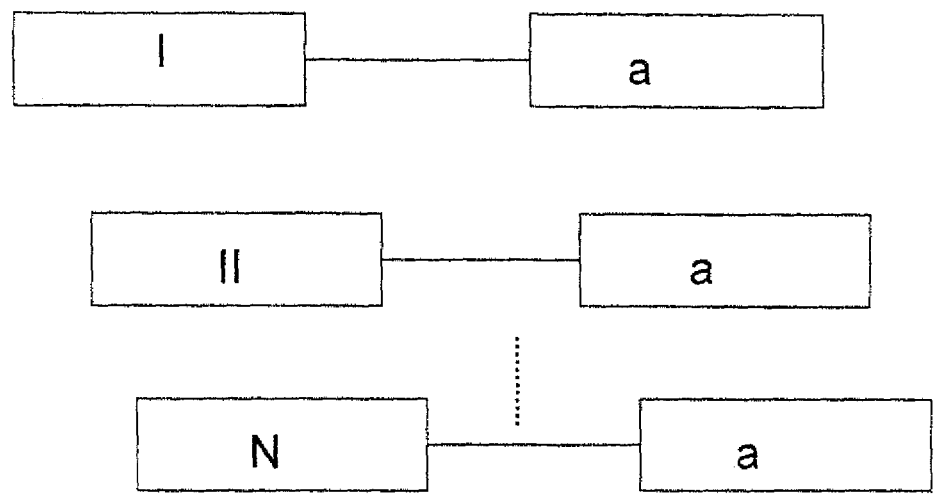
Figure 6D:
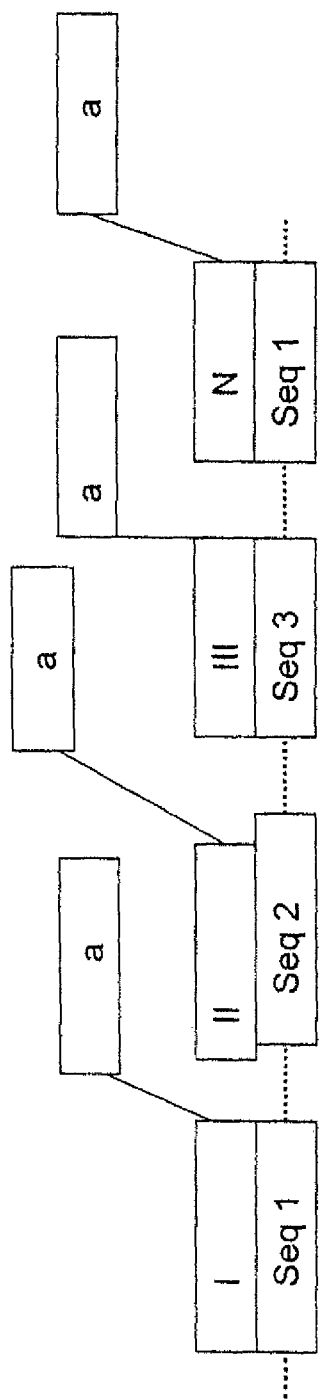
Figure 6E:
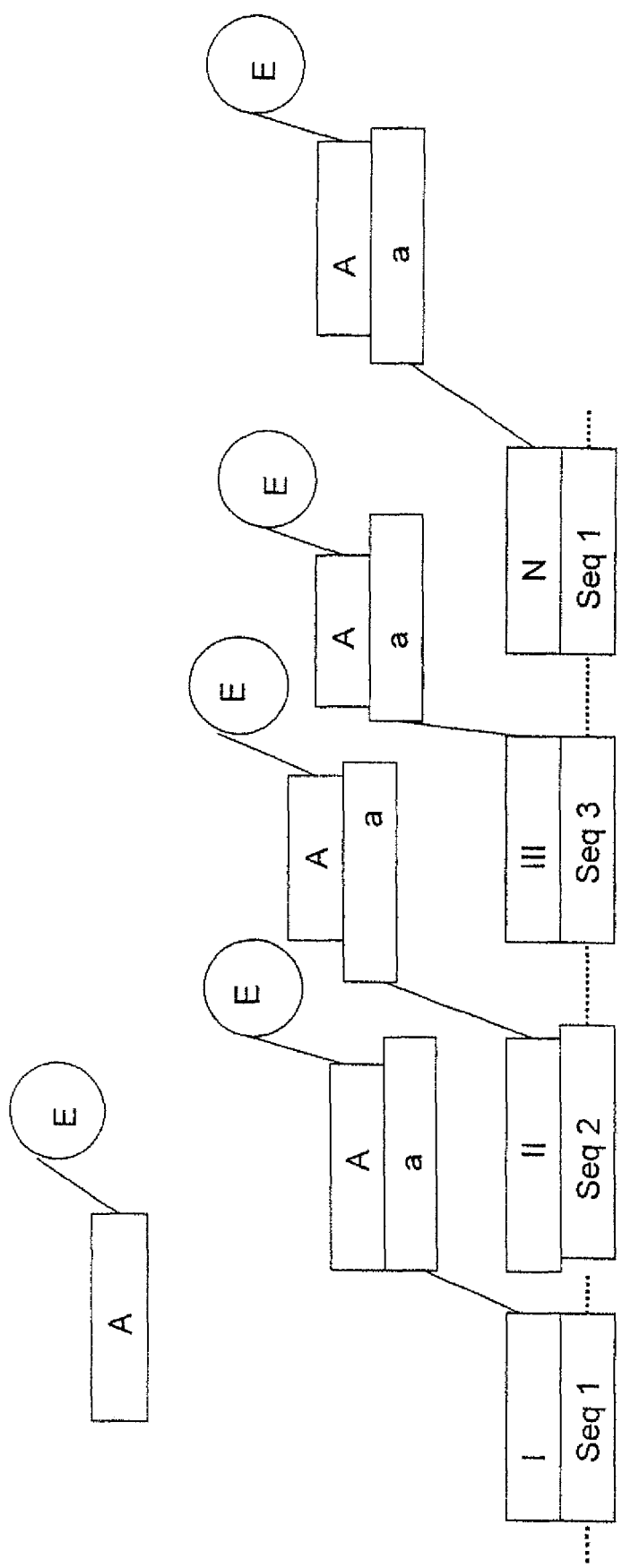
Figure 6F:
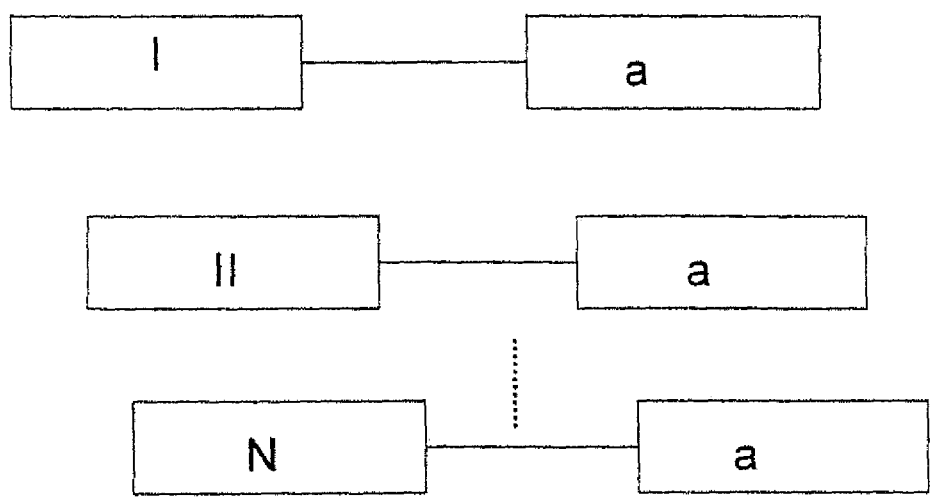
Figure 6G:
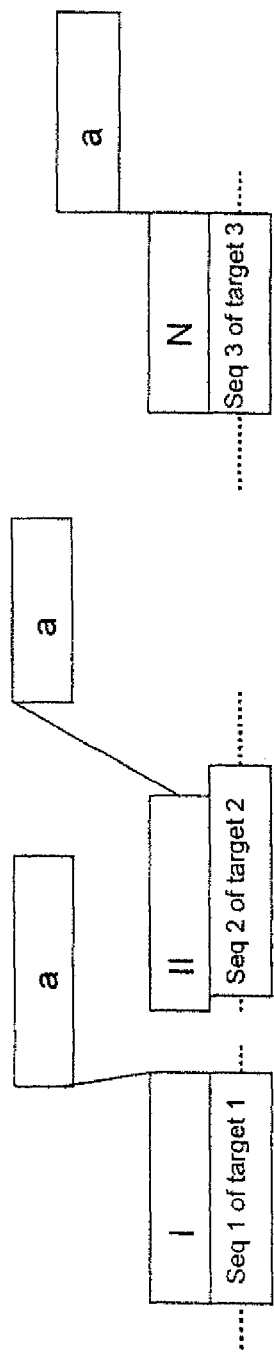
Figure 6H:
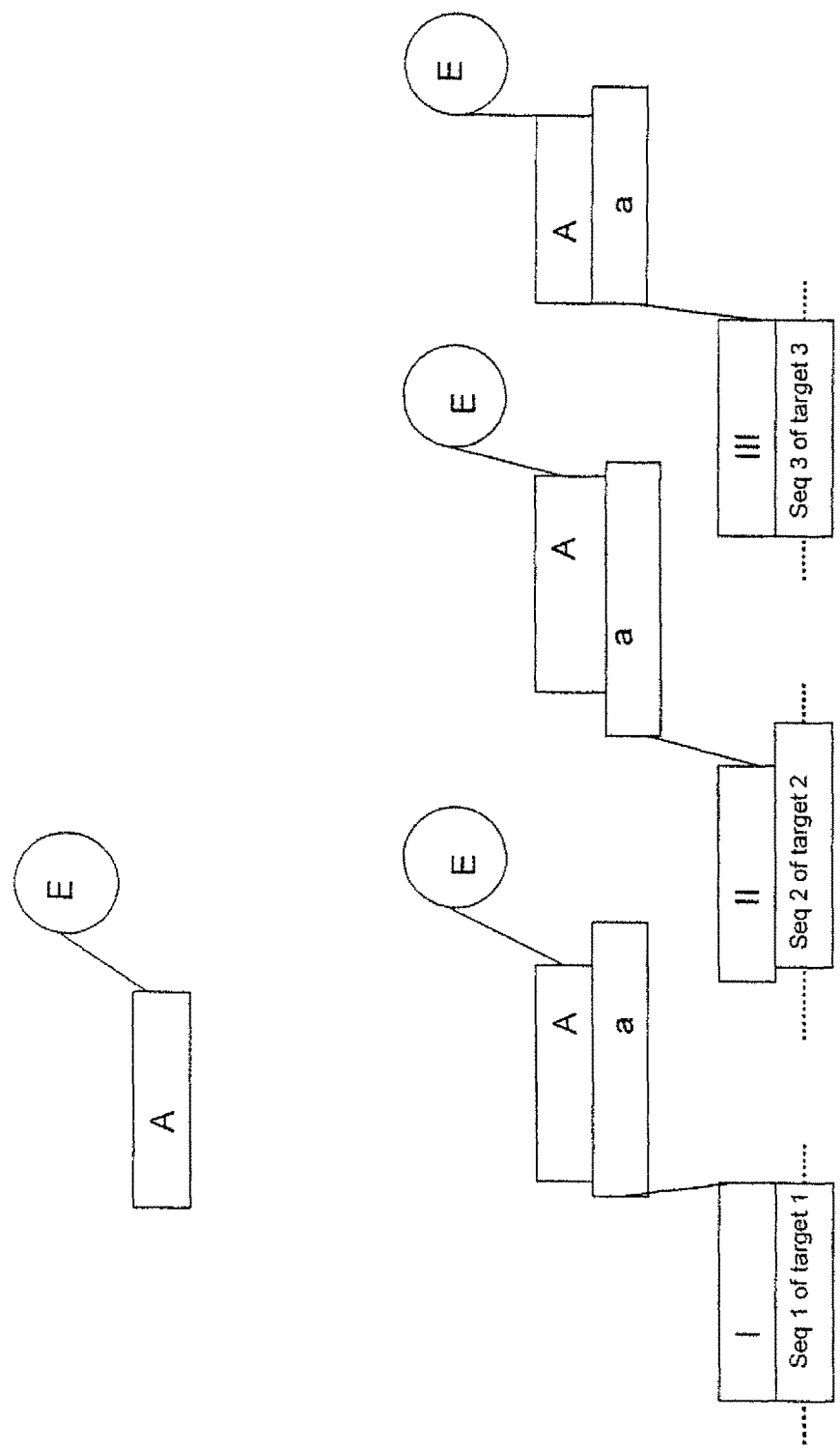

FIGS. 6A-6H show different examples of pre-reporting carriers for use in nucleic acid target detection. For example, as shown in FIGS. 6A and 6B, a pre-reporting carrier can comprise unique target binding regions (e.g., I to N), each with a unique tag (e.g., a1 to a3). Each of the unique tags would be bound by a different reporting carrier. One advantage of this variation is that the pre-reporting carriers (and thus, also, the corresponding reporter carriers) bind at different target locations. This reduces the risk of false positives resulting from mis-binding of the pre-reporter or reporter carrier to the wrong reaction spots. FIG. 6C shows an example where unique target binding regions (I-N) each carry the same tag ("a"). As shown in FIGS. 6D-6F, each pre-reporter carrier could hybridize to part of the same target with detection using a single species of reporter carrier bearing a proficient enzyme conjugate. In further examples, each pre-reporter carrier with the same tag ("a") can bind to different targets as opposed to different parts of the same target (FIGS. 6F-6H).

"Antibody" refers to any immunoglobulin or intact molecule as well as to fragments thereof that bind to a specific epitope that may be used in the practice of the present invention. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term and may be used in the practice of this invention, including IgA, IgD, IgE, IgG, and IgM.

An "antibody fragment" refers specifically to an incomplete or isolated portion of the full sequence of the antibody which retains the antigen binding function of the parent antibody and may also be used in the present invention. Examples of antibody fragments include Fab, Fab', F(ab')2, and Fv fragments; diabodies; linear antibodies; single-chain antibody molecules; and multispecific antibodies formed from antibody fragments.

An intact "antibody" for use in the invention comprises at least two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature, 341:544-546 (1989)), which consists of a VH domain; and (vi) an isolated complementarity determining region (CDR).

"Single chain antibodies" or "single chain Fv (scFv)" may also be used in the present invention. This term refers to an antibody fusion molecule of the two domains of the Fv fragment, VL and VH. Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

A "monoclonal antibody" may be used in the present invention. Monoclonal antibodies are a preparation of antibody molecules of single molecular composition. A monoclonal antibody composition displays a single binding specificity and affinity for a particular epitope.

Non-limiting examples of the specificity of antibodies that may be used in the practice of the invention include those specific for particular antigens; methylation specific antibodies for the detection of methylated DNA; and phosphorylation specific antibodies for the detection of phosphoproetins, among others. For example, virus specific antibodies can be used to detect the presence of virions in samples. All of the antibodies and fragments described above can be modified with groups that allow an antibody or fragment to be attached to a proficient enzyme.

In some embodiments, a nucleic acid is used as a carrier. If a nucleic acid is used, an oligonucleotide with a sequence complementary to at least part of a target nucleic acid can be used. Methods for synthesizing nucleic acids are well known in the art. Nucleic acids of the invention may be modified with groups that allow the nucleic acid to be attached to a proficient enzyme. Mismatches of one or a few selected bases of the carrier nucleic acid to the target may be introduced. Utilizing the artificially introduced mismatch(es), the binding energy could be adjusted to design or engineer selectivity of the carrier over different samples as the result of enthalpy and entropy change.

In addition to oligonucleotides comprising natural bases, oligonucleotides comprising nucleotide analogues may be used, such as peptide nucleic acids (PNAs) or locked nucleic acids (LNAs). In contrast to DNA and RNA, the backbone of PNAs are composed of repeating N-(2-aminoethyl)-glycine units linked by peptide bonds. A locked nucleic acid (LNA) is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in A-form duplexes. LNA nucleotides can be mixed with DNA or RNA residues in an oligonucleotide as needed. Such oligomers can be synthesized chemically and are commercially available.

B. Proficient Enzymes or Carrier Enzymes

The carriers described above can be associated noncovalently or covalently with various proficient enzymes or carrier enzymes in the practice of the invention. Enzymes particularly useful in the practice of the present invention are characterized by reaction rates which approach the diffusion limit of the substrate. A proficient enzyme of the invention typically can have a turnover constant of $10^3$ per second per enzyme to $10^8$ or higher per second per enzyme.

Examples of suitable proficient enzymes or carrier enzymes are included in the following EC classes, but are not limited to, oxidoreductase (EC 1), hydrolase (EC3), lyases (EC4), or ligases (EC6), or an enzyme, enzyme-like nucleic acid, or enzyme-like catalyst that catalyzes a reaction that produces a proton concentration.

Examples of such enzymes are known in the art. Examples of enzymes useful in the practice of the present invention and their characteristics and substrates include, but are not limited to, those shown below.

1. Urease
EC Number: 3.5.1.5, Hydrolase
a. Turnover number: $2.97 \times 10^3$ $S^{-1}$
b. Substrate: Urea
Ref1: PDB: 1fwj.
Ref2: Pearson, M. A. et al, <Kinetic and Structural Characterization of Urease Active Site Variants>Biochemistry, 2000, 39(29) p 8575-8584
2. Phosphocholine Phosphatase
EC number: 3.1.3.75 aka phosphoethanolamine
Spec: Pseudomonas aeruginosa PA5292 gene in PAO1 genome wild-type (construct with truncation and modification in the plasmid construct)
a. Turnover number: $5\text{-}7 \times 10^6$ $S^{-1}$
b. Substrate: p-nitrophenyl phosphate
c. Product: p-nitrophenol
Ref 1: Beassoni, P. R. et al. Current Microbiology, 2006 52(6), p 534-539
3. Beta-Galactosidase
EC number: 3.2.1.23 from *Kluyveromyces marxianus*
a. Turnover number: $2.7 \times 10^6$ $S^{-1}$
b. Substrate: 4-nitrophenyl-beta-D-galactoside
Ref 1: Oconnell, S. et. al. Applied Biochemistry and Biotechnology 2007 V141(1) p 1-13

4. Xylose Reductase
EC number: 1.1.1.307 from *Talaromyces emersonii*
a. Turnover number: $1\text{-}3 \times 10^5$ $S^{-1}$
b. Substrate: D-Xylose, NADPH
Ref 1: Fernandes, S, et al. J. Biosci. 34(6) 2009 p 881-890
5. Shikimate Dehydrogenase
EC 1.1.1.25 *Escherichia coli*
Species: Wild type (shikimate), Mutant S22A, Y39F, D107A, S67A, T106A
a. Turnover number: $1 \times 10^5$ $S^{-1}$
b. Substrate: Shikimate, or quinate, orNAD+
Ref 1: Lindner, H. A. J. Bio. Chem. 2004 V280, P 7162-7169
6. Malate Dehydrogenase
EC number: 1.1.1.37 *Triticum aestivum* or *Talaromyces emersonii*
a. Turnover number: $1 \times 10^5$ $S^{-1}$ b. Substrate: NADH
Ref 1: Maloney, A. P. et al. Eur. J. Biochem 271 2004 p 3115-3126
7. Neopullulanase
EC number: 3.2.1.135 from *Geobacillus stearothermophilus*
a. Turnover number: $1 \times 10^5$ $S^{-1}$
b. Substrate: Starch (Pullulan film aka E1204)
Ref 1: Zareian, S et al., Enzyme Microb. Technol. 2010 46 p 57-63
8. Subtilisin
EC number: 3.4.21.62 from *Bacillus* sp.
a. Turnover number: $1 \times 10^5$ $S^{-1}$
b. Substrate: Suc-Ala-Ala-Pro-Phe-p-nitroanilide
Ref 1: Toogood, H. S. Biochem. J. 2000 250, p 321-328
9. 4-phytase
EC number; 3.1.3.26 from *Aspergillus fumigatus*
a. Turnover number: $3.5\text{-}4.1 \times 10^5$ $S^{-1}$
b. 4-nitrophenyl phosphate or myo-inositol hexakisphosphate
Ref 1: Rodriguez, E. et al. Biochem Biophys Res Commun. 2000 268(2) p 373-378
10. Acetylcholinesterase
EC number: 3.1.1.7
a. Turnover number: $1.4 \times 10^5$ $S^{-1}$
b. Substrate: acetylcholine
Ref 1: Rothenberg M. A. et al. J. Biol. Chem. 168 (1) p 223-231
11. Laccase
EC number: 1.10.3.2 from Basidiomycota
a. Turnover number: $0.6 \times 10^5$ $S^{-1}$
b. substrate: 2,2'-azinobis(3-ethylbenzothiazoline-6-sulfonic acid)
Ref 1: Jordaan, J. et. al., Enzyme Microb. Technol. 2004 V34, P635-641
12. bacterial leucyl aminopeptidase
EC number: 3.4.11.10 from *Fasciola hepatica*
a. Turnover number: $0.3 \times 10^6$ $S^{-1}$
b. Substrate: L-Cys-7-amido-4-methylcoumarin
Ref 1: Acosta, D. et al. Molecular and Biochem. Parasitology 2008, V158(1) p 52-64.
13. Tripeptidyl-peptidase
EC Number: 3.4.14.9 from *Dictyostelium discoideum*
a. Turnover number: $0.55 \times 10^6$ $S^{-1}$
b. Substrate: Ala-Ala-Phe-p-nitroanilide
Ref 1: Krimper, R. P. Biochem and Molecular Biology International 1999 47(6) p 1079-1088
14. coagulation factor VIIa
EC number: 3.4.21.21 from *homo sapiens*
a. Turnover number: $0.35 \times 10^6$ $S^{-1}$
b. Substrate: N-methylsulfonyl-D-Phe-Gly-Arg-p-nitroanilide
Ref 1: Neuenschwander, P. F. et al. Biochemistry 2002 41 p 3364-3371

15. Trypsin
EC number: 3.4.21.4 from *Periplaneta Americana*
a. Turnover number: $0.91 \times 10^6$ $S^{-1}$
b. Substrate: o-aminobenzoyl-AGSRGAGQ-(2,3-dinitrophenyl-ethylene diamine)
Ref 1: Marana, S. R. et al. Biochemical and Biophysical Research Communications 2002 290 p 494-497
16. Beta-fructofuranosidase
EC number: 3.2.1.26 from *Thermotoga neapolitana*
a. Turnover number: $0.73 \times 10^6$ $S^{-1}$
b. Substrate: sucrose
Ref 1: Dipasquale, L. et al. Extremophiles 2009 13 p 345-354

The sensitivity and specificity of the analyte detection could be further improved by utilizing a temperature jump or gradient. Some of the most stable enzymes require higher temperature for optimized activity or as a trigger to activate the enzymes. The reaction temperature therefore could be higher than room temperature, at which temperature, the reaction is still viable. When the temperature is lower than the optimized region, the activity of the enzyme is greatly reduced. The reaction contaminants or background molecules from the sample could be removed or neutralized first before raising the temperature of the optimized zone. One of the reaction contaminants could be dissolved carbon dioxide in the solution, which is an interference to pH variation. Raising temperature will reduce the solubility of the carbon dioxide therefore reduce the interference. The temperature could be raised by a physical method such as concentrated solar power or by exothermic chemical method such as enthalphy change of solvation of magnesium sulphate or calcium chloride, or by a electrical method such as by heat pump. One example of the heat pump is a Peltier device. By the same token, the reaction rate could also be deliberately reduced to optimize the reaction by reducing the temperature. One example of the chemical method is the solvation of ammonium nitrate. A heat pump could be used to reduce the temperature by switching the electrical polarity. In some embodiments, the reaction temperature is from about 4° C., 10° C., 20° C., 30° C., 40° C., 50° C., 60° C., 70° C., 80° C., 90° C., to about 95° C., or higher while still maintaining enzyme activity, or any temperature between the said temperatures.

In addition to the enzymes and substrate systems shown above, the present invention can utilize one or two or more additional pro-enzymes (B, C, D, or more). In such embodiments, pro-enzyme B as a substrate could be activated by an enzyme cassette A in the reporting group. Once enzyme B is activated, enzyme B can further activate enzyme C, which will activate enzyme D and so on. The effective turnover constant in such linked systems is the multiple of the turnover constant of each activated pro-enzyme. For example, the turnover constant of each enzyme (B, C, D, and more) could be as low as 10 or 102 per second per enzyme. However, the multiplied turnover number would be more than 104 per second per enzyme. An example includes the blood-clotting cascade, where activated factor Xa activates thrombin, which activates fibrin from fibrinogen. The activated thrombin also activates factor Xa via factor VIIIa and IXa.

C. Formation of Reporter Carrier

The carrier can be associated with a proficiency enzyme or carrier enzyme either noncovalently or covalently. Examples of conjugation include, but are not limited to, cloning and expressing chimeric proteins as a carrier; use of chemically modifying carbodiimide-NHS reaction, S-Au complex, Tosyl-amine reaction, formaldehyde conjugation, disulfide bonding, molecular imprinting, and site-directional conjugation or random conjugation using any of these methods; and non-covalently: through chimera biotin-avidin or thrombin-hirudin association.

Further examples of coupling or cross linking chemistry that may be used to link two molecules of interest in a process, often referred to as bioconjugation, are known in the art. Common coupling chemistries utilize amine coupling of lysine amino acid residues (typically through amine-reactive succinimidyl esters) and sulfhydryl coupling of cysteine residues (via a sulfhydryl-reactive maleimide). Other linkages can be generated by cycloaddition reactions or "click chemistry". See., e.g., Bioconjugation Techniques, Greg. T. Hermanson, Academic Press, 1996; "Advances in Bioconjugation", Kalia, J. and Raines, R.T., Current Organic Chemistry, 14: 138-147 (2010).

Alternatively, the carrier may be made as a fusion protein using standard molecular biology and protein purification techniques if two proteins are joined. Once sequences encoding a desired fusion protein have been prepared, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ(*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 *Streptomyces*), YIp5 (*Saccharomyces*), YCp19 (*Saccharomyces*) and bovine papilloma virus (mammalian cells). See, Sambrook et al., supra; DNA Cloning, supra; B. Perbal, supra. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence can or can not contain a signal peptide or leader sequence. Leader sequences can be removed by the host in post-translational processing. See, e.g., U.S. Pat. Nos. 4,431,739; 4,425,437; 4,338,397.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli*, *Bacillus subtilis*, and *Streptococcus* spp., will find use with the present expression constructs. Yeast hosts useful in the present invention include, but are not limited to, *Saccharomyces cerevisiae*, *Candida albicans*, *Candida maltosa*, *Hansenula polymorpha*, *Kluyveromyces fragilis*, *Kluyveromyces lactis*, *Pichia guillerimondii*, *Pichia pastoris*, *Schizosaccharomyces pombe* and *Yarrowia lipolytica*. Insect cells for use with baculovirus expression vectors include, but are not limited to, *Aedes aegypti*, *Autographa californica*, *Bombyx mori*, *Drosophila melanogaster*, *Spodoptera fmgiperda*, and *Trichoplusia ni*.

Capture Component

A capture component can be immobilized to the surface of a membrane for the capture of reporter carrier-target complexes. The capture molecule recognizes and forms a complex with the target without preventing the reporter carrier from forming a complex with the same target molecule. Only a reporter carrier that has formed a complex with the target will be immobilized by the capture component. As shown in FIG. 1, immobilization of reporting carrier-target capture component results in the formation of a sandwich structure. The reporting carriers that are not part of the structure are soluble and are removed by flow of liquid or by washing, for example, in a lateral flow format. When a wash solution is used, a buffer having a pH of about 8 to about 9.5 is preferred. The buffering capacity of the buffer must not be greater than the expected pH change when a when a proton producing enzyme and substrate are used. Typical wash buffer solutions would have a concentration of about 0.03 mM to about 0.1 mM. Aqueous, alcohol aqueous and saline buffers comprising tris(hydroxymethyl)aminomethane (Tris) and phosphates are non-limiting examples of suitable buffering solutions. In general, the capture component will be a protein or nucleic acid. The capture component can be immobilized to the surface of a chromatographic medium using methods known in the art. See, e.g., Nakanishi et al., Current Proteomics, 5:161-197 (2008). Methods for immobilization of nucleic acids to surfaces are also known. See, e.g., Wu et al., J. Biomater. Sci. Polymer. Edn., 19: 725-753 (2008). Multiple types of capture components and reporter carriers may be used to detect multiple targets in one test. For example, multiple targets can be multiple nucleic acids or a combination of nucleic acid and non-nucleic acid, e.g., protein targets. Any of a number of immobilization methods, both covalent and non-covalent, known in the art may be used in the practice of the invention.

General Detection Method

FIG. 1 shows the various stages for general target detection, involving sample preparation, reporting carrier attachment to a target, signal carrier-target immobilization, excess reagent wash away, and result display.

Prepare sample: As a first step, sample is prepared for use in the method and device of the present invention. As will be appreciated by one of skill in the art, possible steps within this stage will vary with implementation and target molecule types. Examples of steps that may be used in this stage include, but are not limited to: methods to improve concentration of target molecules, nucleic acid extraction from cells, and purification of sample. In some embodiments, extensively sample preparation is not needed prior to application of the sample (e.g., a liquid sample like blood or urine).

Attach reporting carrier: As shown in FIG. 1, this step uses reporting carrier containing enzyme cassettes. The reporting carrier will form a complex with target molecules of interest.

Immobilize reporting carrier: an immobilizer array of capture components is used to capture the biological targets. As shown in FIG. 1, upon immobilizer capture of a target which is in a complex with a reporting carrier, a sandwich structure of immobilizer-biological targetreporting carrier is formed. In different embodiments, it is possible to have multiple immobilizers (or capture components) in the array for different target molecules.

Wash away excess molecules: This optional step washes away other molecules, excess sample, reporting carriers, or any other molecules which are not captured by the immobilizer arrays. A wash solution is applied upstream of the detection zone such that it migrates by capillary action through the detection zone and the control zone if present to the absorptive pad at the distal end of the test strip. The amount of the optional wash solution depends on the size of the test strip and the nature of the test and is easily determined by one skilled in the technology Display result: The immobilized reporting carrier at this stage is mixed with reagents, generally substrates, which react with a proficient or high yield enzyme in the carrier to rapidly form products which can be observed. One or more enzymes could also be added to accelerate the formation of the products thus forming a reaction cascade. Depending on the selection of the enzymes and reagents, different detection methods can be employed. These include, but are not limited to, for example pH change, color change, density of color change, or light emissions, among others. Substrates are typically applied to the chromatographic test strip by spray, painting, dropper or poured.

Figure 2:
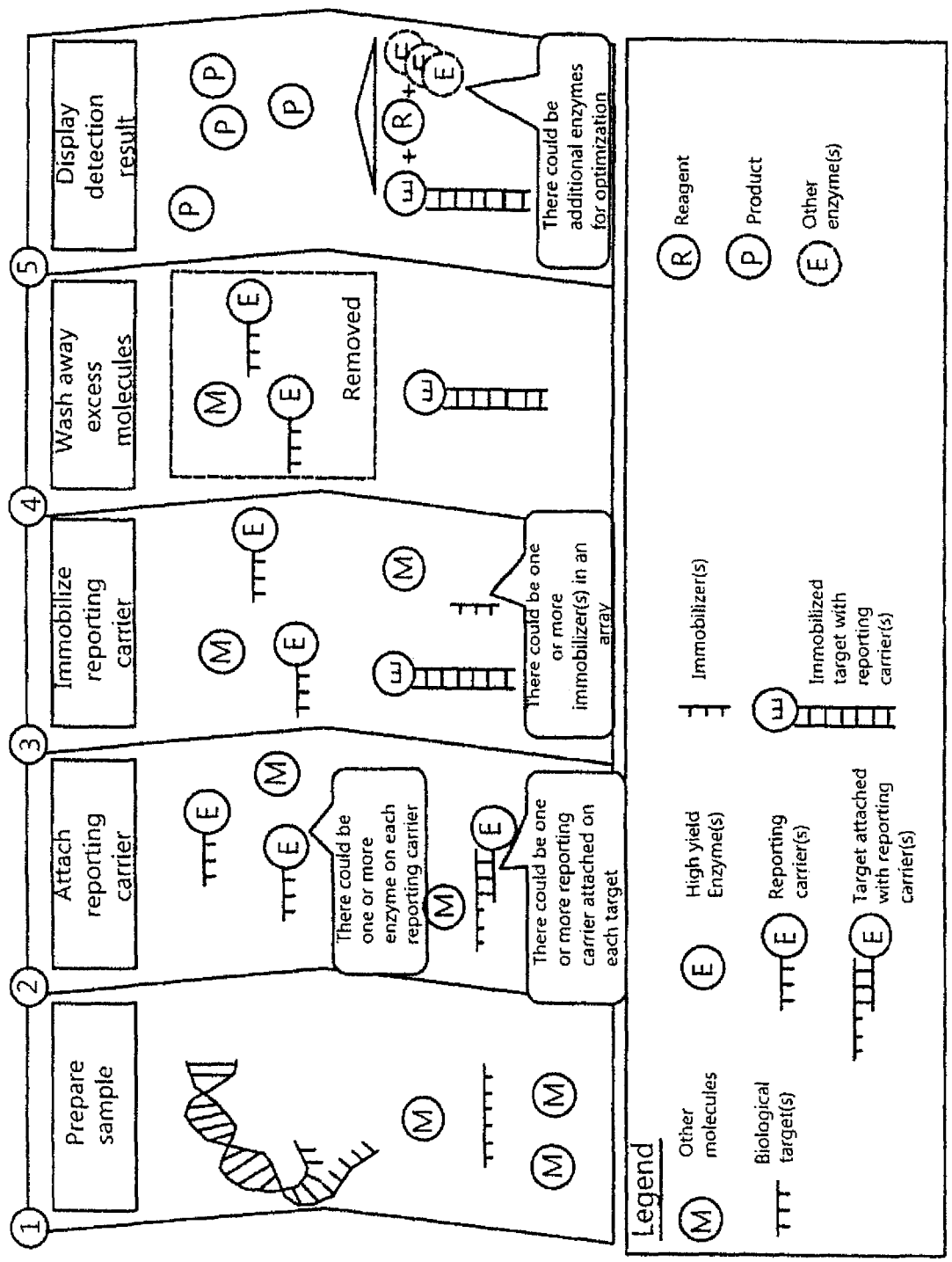
FIG. 2 shows the general steps for nucleic acid detection.

FIG. 2 illustrates the application of the present invention in a nucleic acid test. The general workflow is similar to that shown in FIG. 1, as applied to nucleic acid target molecules.

Prepare sample: For this application, sample preparation could include routine steps such as nucleic acid extraction, sample concentration, RNA extraction, and nuclease inhibition. For some applications, the DNA, e.g., genomic DNA may need to be broken down in size, for instance, by shearing before use in the method.

Attach reporting carrier: In this application, the high proficiency or high yield enzymes are attached to synthesized polynucleotides which form the reporter carrier or enzyme cassette. In some embodiments, there can be more than one polynucleotide for a nucleic acid target. The polynucleotides in the reporter carrier are allowed to hybridize to the target nucleic acid.

Immobilize reporting carrier: As shown in FIG. 2, the immobilizer arrays can comprise one or more polynucleotides which are specific to the target nucleic acid. If there is a match, the immobilizer will hybridize with the target nucleic acid to form a complex of reporting carrier-target-immobilizer. The formation of this complex locks the reporting carriers in place. The selection of polynucleotides in reporting carriers and immobilizers can be used for a variety of applications, including but not limited to, detection of single nucleotide variation, methylation, or sequencing of a target.

Wash away excess molecules: At this stage, the excess molecules and enzyme cassettes are washed away, leaving behind the bound reporting carrier-target complex.

Display signal: The reporting carrier would then be allowed react with substrate reagents to form an observable product. In some embodiments, an additional one or more enzymes could be added to accelerate the reaction.

Lateral Flow Platform

FIG. 3 illustrates implementation of the present invention in a lateral flow platform. It will be appreciated that implementation may vary for different sample types with respect to the location of different components at various sections of the platform for optimal performance. In FIG. 3, The sample pad 1 is upstream of conjugate pad 2 which is upstream of Chromatographic membrane 3 which is upstream of detection zone (Test Line) 4, which is upstream of Control zone (control line) 5, which is upstream of Adsorbent pad 6. The entire devise is on support material 8.

Similar to other forms of lateral flow, the sample can enter the device at a sample pad, and ultimately arrive at the absorbent pad by traveling along the membrane on top of the backing material. The reporting carriers can be deposited in a conjugate pad, and the immobilizer array can be present in sense and control lines. As is easily appreciated, the order of the control and the sense lines can be different, and there can be multiple sense lines in some embodiments. The substrate reagent and additional enzymes (if needed) can also be present in the control and sense lines.

As the sample travels through the conjugate pad, a complex of reporting carrier and the target are formed. When the sample front reaches the sense line, the target, which has formed a complex with the reporting carrier, would be immobilized by the array. Reaction then occurs to form sufficient products that can be monitored. If the immobilized probe (capture component) does not match with a target in the sample, then the sample nucleic acid would flow through the membrane leaving minimal concentration of enzyme at the detection line. A control line acts as the positive control on the device. The positive control demonstrates that the test strip is functional, thereby minimizing false negative test results.

Figure 7:
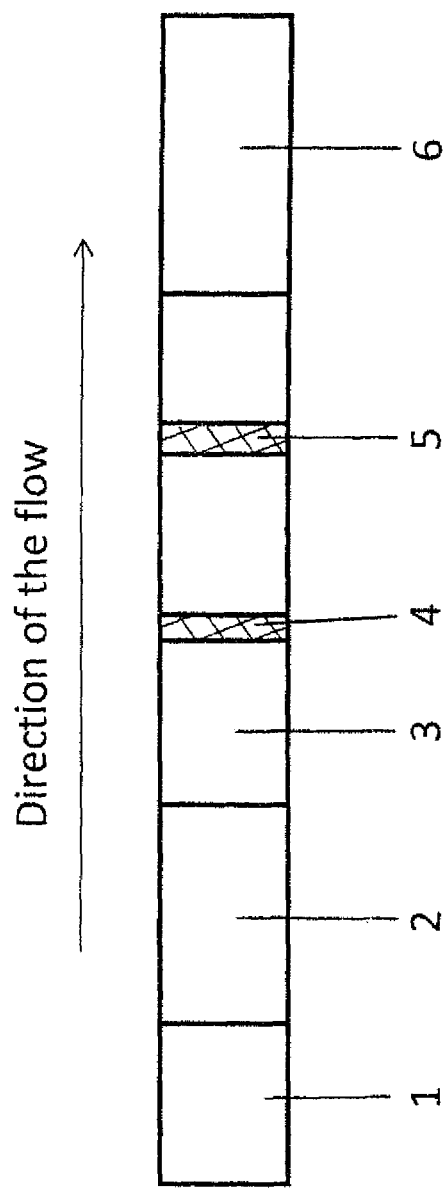
FIG. 7 illustrates a lateral flow device with a positive test result.

FIG. 7 illustrates a positive test result. The detection zone 4 indicates the presence of enzyme indicating that the analyte-reporting carrier complex has been captured in the detection zone. The positive indicator response is the result of substrate being added to the test strip after migration of the test sample past the detection zone. The control zone 5 also indicates the presence of enzyme indicating that the uncomplexed reporting carrier has migrated the length of the test device and has been captured in the control zone providing a change in the indicator after application of the enzyme substrate establishing the presence of the uncomplexed reporting carrier.

Figure 8:
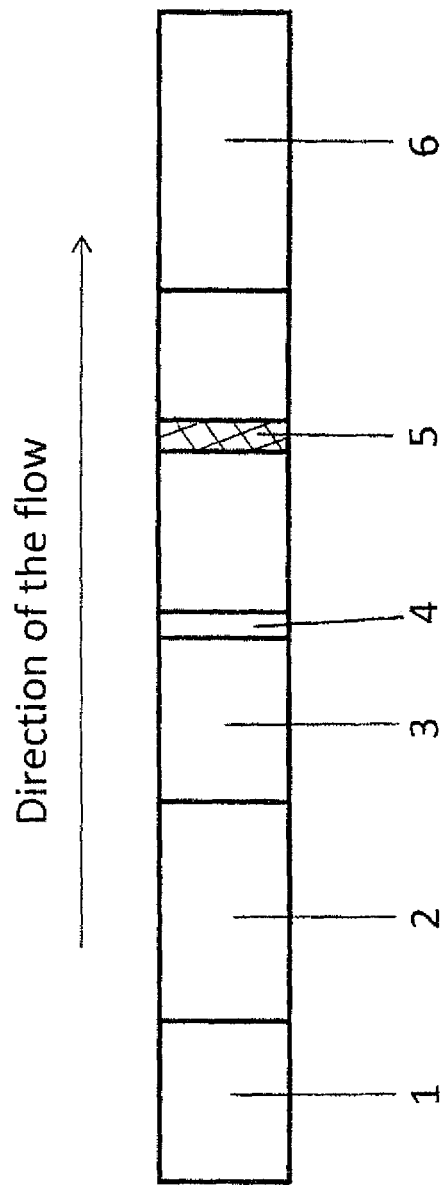
FIG. 8 illustrates a lateral flow device with a negative test result.

FIG. 8 illustrates a negative test result as none of the analyte reporting carrier complex was formed or captured in the detection zone. The positive response indicated in the control zone verifies that the test strip functioned properly and that the exzyme and reporting carrier are present and active.

The following examples of specific aspects for carrying out the present invention are offered for illustrative purposes only, and are not intended to limit the scope of the present invention in any way.

EXAMPLES

Example 1

Embodiments of a Lateral Flow Device

FIG. 4 shows various embodiments of a lateral flow device that can be used in the practice of the present invention. A sample loading zone 1 is provided. Flow in the direction indicated by the arrow results in the interaction of the sample with a reporting carrier 7 found in the reporter carrier loading zone 2. The detection zone 4 contains capture components (upwardly directed solid arrows) and display result materials, such as substrates, and, if necessary, additional pro-enzymes to further amplify the signal. A positive control zone can be provided 5. The supporting scaffold matrix through which the sample moves, if present, can be a. chemical coating or membrane of porous matrix or branched polymers. As shown in FIG. 4B-4D, the scaffold matrix may be mounted on a solid non-porous backing 8, which may be flexible or porous. In some embodiments, the detection zone 1, can contain one type of immobilizer array 8 (such as a antibody, antigen, nucleic acid, etc.) or multiple types of immobilizer array, which may be placed at different spatial locations in the detection zone 4a, 4b, and 4c. FIG. 4E illustrates that inactive pro-enzymes 9, can be present in the immobilizer array, which when activated can lead to a high overall turnover for the system. In further embodiments, the supporting scaffold matrix in the vicinity of the immobilizer array may comprise a pH sensitive material, such as a pH sensitive hydrogel containing 10, for example gold nanoparticles 10a. Such a pH sensitive material may be used to detect the reaction of an enzyme, whose catalytic activity results in a pH change. As shown in FIGS. 4G and 4H, examples of surface pH sensitive display molecules that can be used to practice the present invention include acridine orange, cyanine, liposomes, or fluorescent dextran 11 or a soluble molecule as such as BSA 12.

Example 2

Operation of Embodiments of a Lateral Flow Device

FIG. 5 illustrates operation of various embodiments of the present invention. A sample target 13 can be introduced into a sample loading zone 1 (Step A). Lateral flow in the direction indicated by the arrow can bring the sample target 13 into contact with a reporting carrier 7 (Step B). Further lateral flow carries the complex of sample target and reporting carrier 14 toward a detection zone 5 (Step C). Capture components in the detection zone (upwardly directed solid arrows) immobilize the complex of sample target and reporting carrier 15 (Step D and 4-E). In various embodiments, the capture components may be singular or clusters of variants (compare upwardly directed arrows in Steps D with E). Lateral flow along the capture component and immobilized complex of sample target and reporting carrier removes excess materials such as unbound reporting carriers, unbound sample targets and the like, and serves as a washing step (Step F). In Step G, enzyme substrate and other soluble molecules can be applied to the immobilizer array zone. In various embodiments, the enzyme can be a single proficient enzyme that converts a substrate to product 17, 18, or multiple linked pro-enzymes 19 can be used. A number of possible display options are shown in Steps J-L. For example, detection of reaction product 17 can be indicated through the change of color of a hydrogel, such as a pH sensitive hydrogel containing gold nanoparticles 10, 10b, 21, 22 (Step J). Other display options can rely on a color change (e.g., silver reduction) 11, 23, 24 (Step K). In another embodiment, the pH sensitive precipitation of a soluble molecule such as BSA can be used for visualization 12, 25 (Step L).

In a preferred embodiment of the current disclosure, the device is either a lateral flow unit. The whole device is very low cost, portable, instrument-free, and sensitive. The device is characterized by distinct aspects. One is that the enzyme is attached to the conjugate and the other is that the indicator is printed or immobilized at the detection zones. The product from the enzymatic reaction reacts with the indicator to give visual difference at the detection zones.

The indicator could be pH sensitive which will change color or fluorescence when the protonation status of the indicator changed. In one of the embodiments, the pH indicator has been reacted with a carrier membrane molecule such as cellulose acetate. In another embodiment, the pH indicator is encapsulated in proton permeable plastics ["Full-range optical pH sensor based on imaging techniques", Capel-Cuevas, S., Cuellar, M. P., de Orbe-Paya, I., Pegalajar, M. C., Capitan-Vallvey, L. F., Analytica Chimica Acta, 681 (2010) 71-81. In both cases, the deposition of the pH indicator onto the membrane did not interfere with the conjugate binding in a lateral flow device.

In a preferred embodiment, the indicator is printed or sprayed on to a membrane down stream of the conjugate pad to form a line or a zone. Each line or zone is separated from another line or zone of indicator by a buffering region of membrane without the indictor. The buffering region could also contain a layer of immobilized buffer component to prevent the cross reaction between different lines/zones.

In one embodiment, the dye (bromothymol blue) is prepared mixing bromothymol blue 2.1 mg; tridodecylmethylammonium chloride (TDMAC) 2.8 mg; dioctyl sebacate (DOS) 19.6 mg; ethylenglycol 19.6 mg and tetrhydrofuran (THF) 1 ml. The bromothymol solution has a pH of about 8 to about 9.5. The indicator-polymer solution was spray painted on the membrane using an air brush gun. The airbrush gun is the High Performance C PLUS Airbrush made by Iwata. Only the regions of the control/testing line on the lateral flow strip were coated with the polymer/indicator. After spraying, the whole strip was left at desiccator for 16 hrs before use.

In a preferred embodiment, a pH indicator could be covalently linked with polymers such as cellulose (U.S. Pat. No. 4,029,597). In one embodiment, the pH sensitive dye is specially designed with hydroxysulfonyl end group for covalent chemistry of the dye molecule and cellulose. PH sensitive dye molecule is treated with sulphuric acid at room temperature to form terminal sulfoester groups. Later, the dye solution in sulphuric acid is diluted into de-ionized water and neutralized with sodium hydroxide. Cellulose acetate is added to the solution at this stage. After 5 min, sodium carbonate and in another 5 min sodium hydroxide is added to the solution. The sulfoester group under the strong alkaline conditions form vinyl sulfone end group and cellulose acetate is hydrolysed to form cellulose with terminal hydroxyl groups. Under the same alkaline conditions, vinyl sulfone group on the dye molecule reacts with the hydroxyl groups of cellulose to form a covalent linkage between pH indicator dye and cellulose. The final reaction product is washed with de-ionized water. The pH sensitive cellulose is dissolved in solvent to prepare 10% wt solution. Aqueous solution is preferred. Indicator solution is spray coated on the nitrocellulose membrane to have pH indicator dye immobilization on the lateral flow device.

A preferred substrate solution for the carboxylesterase enzyme comprises the following formula:
10 mM allyl hexanoate
0.1 mM Tris pH 8.5
5% isopropanol The substrate is the allyl hexanoate. Upon hydrolysis, one allyl hexanoate molecule produces one hexanoic acid and one 2-propenol. The starting pH of the reaction is defined by the 0.1 mM Tris at pH 8.5. The buffer capacity of the substrate solution would be less than 50 micro molar. The overall proton balance at pH 8.5 would produce proton surplus, such that the pH value would be reduced as the result of the hydrolysis.

The change in pH as a result of hydrolysis will cause the indicator of for example bromothymol blue as described above to change color from blue to yellow.

In a preferred embodiment, the device is protected from the carbon dioxide in the air, which would gradually move solution pH toward pH 6.5. The protection could be done by lamination or housing.

Preferred carriers are micro particles having diameters from about 10 nm to about 500 nm. Preferably the particles will have diameters from about 10 nm to about 100 nm. Preferred particles are of latex or gold. The particles are coated with material the proficient enzyme can bond or complex with. A preferred coating is streptavidin. A preferred particle is a 20 nm gold particles with streptavidin coating. A preferred enzyme is carboxylesterase. Preferred substrates for carboxylesterase are phenethyl butyrate in 0.1 mM Tris buffer at pH 8 and 10 nM allyl hexanoate in 0.1 mM Tris pH 8.5 buffer in 5% isopropanol.

A preferred particle composition is a 40 nm Innovacoat gold particle coated with Streptavidin by the following protocol:
1. Prepare 0.2 mg/mL streptavidin solution in phosphate buffer, pH 7.4
2. Mix 42 µL of the reaction buffer from the Innovacoat Gold kit <http://www.innovabiosciences.com/gold-conjugation-kits/innovacoat-gold.html> (20OD 40 nm), with 12 µL of the streptavidin solution
3. Transfer 45 µL of the mixture to one portion of the Innovacoat gold.
4. Incubate at room temperature for 10 mins before stopped by 5 µL of the quencher in the kit.
5. Spin down the particle and remove the supernatant
6. Resuspend with 100 µL PBS buffer
7. Repeat step 5
8. Resuspend in 50 µL PBS and add to final 0.1% BSA and 0.01% (20K MW) polyethylene glycol
9. Mix 1 uL of biotinylated antibody(about 12 µg/mL), 2 µL of biotinylated carboxylesterase (about 7 ug/ml), 2 µL of the Streptavidin modified Innovacoat gold to form the reporting carrier ie conjugate.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

We claim:

1. A lateral flow assay device for detecting the presence of an analyte within a test sample, the lateral flow assay device comprises:
   a chromatographic medium that includes:
      a sample loading zone located upstream of a detection zone;
      a reporting carrier zone located between the sample loading zone and a detection zone, wherein said reporting carrier zone comprises a reporting carrier capable of forming a complex with the analyte, and wherein said reporting carrier comprises a carrier and at least one proficient enzyme;
      a detection zone, wherein the detection zone comprises a capture component for the analyte, and an indicator for indicating the presence or absence of a product from a reaction of the proficient enzyme and a substrate thereby indicating the presence or absence of the analyte; and
      a control zone, wherein the control zone comprises a further capture component for the uncomplexed reporting carrier from the detection zone, and a further indicator for indicating the presence or absence of a product from a reaction of the proficient enzyme and the substrate thereby indicating the presence or absence of uncomplexed reporting carrier.

2. The lateral flow assay device of claim 1, wherein the carrier comprises an antibody or a nucleic acid.

3. The lateral flow assay device of claim 2, wherein the antibody interacts non-covalently with the proficient enzyme to form a proficient enzyme conjugate, or wherein the nucleic acid is covalently attached to the proficient enzyme to form a proficient enzyme conjugate.

4. The lateral flow assay device of claim 2, wherein the antibody interacts noncovalently with the proficient enzyme.

5. The lateral flow assay device of claim 2, wherein the antibody or nucleic acid is covalently attached to the proficient enzyme.

6. The lateral flow assay device of claim 1, wherein the proficient enzyme is selected from the group consisting of: urease, phosphocholine phosphatase, betagalactosidase, xylose reductase, shikimate dehydrogenase, malate dehydrogenase, carboxylesterase, neopullulanase, subtilisin, 4-phytase, acetylcholinesterase, laccase, bacterial leucyl aminopeptidase, tripeptidyl-peptidase I, coagulation factor VIIa, trypsin, and beta-fructofuranosidase.

7. The lateral flow assay device of claim 1, wherein the detection zone further comprises one or more inactive pro-enzymes as substrates.

8. The lateral flow assay device of claim 1, wherein the indicator is a pH sensitive indicator.

9. The lateral flow assay device of claim 8, wherein the pH sensitive indicator is potassium 1-hydroxy-4-[4-(2-hydroxyethylsulphonyl)phenylazo]-naphthalene-2-sulphonate.

10. The lateral flow assay device of claim 8, wherein the pH sensitive indicator is a pH sensitive cellulose acetate coupled dye.

11. The lateral flow assay device of claim 1, wherein the reporting carrier zone comprises a conjugate pad.

12. The lateral flow assay device of claim 1, wherein the sample loading zone comprises a sample loading pad.

13. The lateral flow assay device of claim 1, further comprising a rigid or flexible backing material.

14. The lateral flow assay device of claim 1, wherein the presence of the product of the proficient enzyme and substrate is indicated by a pH change.

15. The lateral flow assay device of claim 14, wherein the pH change is determined using a pH sensitive hydrogel.

16. The lateral flow assay device of claim 1, wherein the presence of the product of the proficient enzyme and substrate is indicated by a colorimetric change.

17. The lateral flow assay device of claim 16, wherein the colorimetric change is due to silver ion reduction.

18. The lateral flow assay device of claim 1, wherein the presence of the product of the proficient enzyme and substrate is indicated by fluorescence emission.

19. The lateral flow assay device of claim 1, wherein the presence of the product of the proficient enzyme and substrate is indicated by electrochemical methods.

20. The lateral flow assay device of claim 1, wherein the presence of the product of the proficient enzyme and substrate is indicated by precipitation of a soluble component.

21. The lateral flow assay device of claim 20, wherein the soluble component is a protein or pH sensitive polymer.

22. The lateral flow assay device of claim 21, wherein the protein is BSA.

23. The lateral flow assay device of claim 21, wherein the pH sensitive polymer is selected from the group consisting of methyl acrylic acid, methyl methacrylate, methacrylic acid 2-(dimethylamino) ethyl ester, and N-hydroxymethyl acrylamide.

24. The lateral flow assay device of claim 1, further comprising an absorptive pad at the distal end of the chromatographic medium.

25. The lateral flow assay device of claim 1, wherein the substrate is allyl hexanoate and the proficient enzyme is carboxylesterase.

26. A lateral flow assay kit for detecting the presence of an analyte within a test sample, comprising the lateral flow assay device according to claim 1 and
a substrate for the proficient enzyme; wherein the substrate can be applied to the detection zone after the test sample has been allowed to flow through the lateral flow device and the product of the enzyme and substrate can be detected.

27. The lateral flow assay kit of claim 26, wherein the carrier comprises an antibody.

28. The lateral flow assay kit of claim 27, wherein the antibody is associated with the proficient enzyme by a noncovalent interaction.

29. The lateral flow assay kit of claim 26, wherein the carrier comprises a nucleic acid.

30. The lateral flow assay kit of claim 26, wherein the proficient enzyme is selected from the group consisting of: urease, phosphocholine phosphatase, betagalactosidase, xylose reductase, shikimate dehydrogenase, malate dehydrogenase, carboxylesterase, neopullulanase, subtilisin, 4-phytase, acetylcholinesterase, laccase, bacterial leucyl aminopeptidase, tripeptidyl-peptidase I, coagulation factor VIIa, trypsin, beta-fructofuranosidase.

31. The lateral flow assay kit of claim 26, wherein the carrier comprises an antibody and the antibody interacts non-covalently with the proficient enzyme to form a proficient enzyme conjugate.

32. The lateral flow assay kit of claim 26, wherein the carrier comprises a nucleic acid and the nucleic acid is covalently attached to the proficient enzyme to form a proficient enzyme conjugate.

33. The lateral flow assay kit of claim 26, further comprising one or more inactive pro-enzymes in the detection zone.

34. The lateral flow assay kit of claim 26, wherein the activity of the proficient enzyme conjugate is detectable by monitoring the effect of a reaction assisted by the proficient enzyme.

35. The lateral flow assay kit of claim 26, wherein the indicator is a pH sensitive indicator.

36. The lateral flow assay kit of claim 35, wherein the pH sensitive indicator is Potassium I-hydroxy-4-[1-(2-hydroxyethylsulphonyl)phenylazo]-naphthalene-2-sulphonate.

37. The lateral flow assay kit of claim 35, wherein the indicator is a pH sensitive cellulose acetate coupled dye.

38. The lateral flow assay kit of claim 26, wherein the reporting carrier zone comprises a conjugate pad.

39. The lateral flow assay kit of claim 26, wherein the sample loading zone comprises a sample loading pad.

40. The lateral flow assay kit of claim 26, further comprising a rigid or flexible backing material.

41. The lateral flow assay kit of claim 26, wherein the carrier comprises an antibody or nucleic acid that is covalently attached to the proficient enzyme.

42. The lateral flow assay kit of claim 26, further comprising a source of one or more inactive pro-enzymes.

43. The lateral flow assay kit of claim 26, wherein the detection zone detects a product of the proficient enzyme by detection of a pH change.

44. The lateral flow assay kit of claim 43, wherein the pH change is detected using a pH sensitive hydrogel.

45. The lateral flow assay kit of claim 26, wherein the detection zone detects the product of the proficient enzyme by colorimetric change.

46. The lateral flow assay kit of claim 26, wherein the detection zone detects the product of the proficient enzyme by fluorescence emission.

47. The lateral flow assay kit of claim 26, wherein the detection zone detects the product of the proficient enzyme by an electrochemical method.

48. The lateral flow assay kit of claim 47, wherein the electrochemical method produces a colorimetric change that is due to silver ion reduction.

49. The lateral flow assay kit of claim 26, wherein the detection zone detects the product of the proficient enzyme by precipitation of a soluble component.

50. The lateral flow assay kit of claim 49,
wherein the soluble component is a protein or pH sensitive polymer.

51. The lateral flow assay kit of claim 50, wherein the soluble component is BSA protein.

52. The lateral flow assay kit of claim 50, wherein the soluble component is a pH sensitive polymer that is selected from the group consisting of methyl acrylic acid, methyl methacrylate, methacrylic acid 2-(dimethylamino) ethyl ester, and N-hydroxymethyl acrylamide.

53. The lateral flow assay kit of claim 26, further comprising an absorptive pad at a distal end of the chromatographic medium.

54. The lateral flow assay kit of claim 26, wherein the substrate is allyl hexanoate and the proficient enzyme is carboxylesterase.

55. A method of detecting an analyte in a test sample, the method comprising
   i) providing the lateral flow assay device according to claim 1;
   ii) adding a pre-reporting carrier to the test sample;
   iii) contacting the sample loading zone with the test sample, wherein the test sample travels through the reporting carrier zone along the chromatographic medium from the sample loading zone to the detection zone and beyond the detection zone;
   iv) adding a substrate to the detection zone, wherein the substrate undergoes a reaction in the presence of the reporting carrier-analyte complex; and
   v) generating a response of the indicator within the detection zone that corresponds to the presence or absence of the analyte in the test sample.

56. The method of claim 55, further comprising adding a further substrate to the control zone of the lateral flow assay device, wherein the further substrate undergoes a reaction in the presence of the uncomplexed reporting carrier; and generating a response of the indicator within the control zone that corresponds to the presence or absence of the uncomplexed reporting carrier.

57. The method of claim 55, further comprising maintaining a reaction temperature in the reaction zone in a range from 4° C. to 95° C.

58. The method of claim 55, wherein the analyte is selected from the group consisting of a protein or a nucleic acid.

59. The method of claim 55, wherein the carrier in the lateral flow assay device comprises an antibody or a nucleic acid, or wherein the proficient enzyme in the lateral flow assay device is selected from the group consisting of urease, phosphocholine phosphatase, betagalactosidase, xylose reductase, shikimate dehydrogenase, malate dehydrogenase, carboxylesterase, neopullulanase, subtilisin, 4-phytase, acetylcholinesterase, laccase, bacterial leucyl aminopeptidase, tripeptidyl-peptidase I, coagulation factor VIIa, trypsin, and beta-fructofuranosidase.

60. The method of claim 59, wherein the carrier and the proficient enzyme form a proficient enzyme complex, and wherein the carrier is selected from the group consisting of (a) an antibody that interacts non-covalently with the proficient enzyme to form the proficient enzyme conjugate; (b) a nucleic acid that is covalently attached to the proficient enzyme to form the proficient enzyme conjugate; or (c) an antibody that is covalently attached to the proficient enzyme to form the proficient enzyme conjugate.

61. The method of claim 60, wherein the activity of the proficient enzyme conjugate is detected by monitoring the effect of a proficient enzyme assisted reaction.

62. The method of claim 61, wherein an effect of the proficient enzyme assisted reaction is proton release.

63. The method of claim 62, wherein the proton release produces a pH change and wherein the pH change is determined using a pH sensitive indicator.

64. The method of claim 63, wherein the pH sensitive indicator is potassium 1-hydroxy-4-[4-(2-hydroxyethylsulphonyl)phenylazo]-naphthalene-2-sulphonate or a pH sensitive cellulose acetate coupled dye.

65. The method of claim 60, wherein the activity of the proficient enzyme conjugate is indicated from the group consisting of colorimetric change, fluorescence emission, or electrochemical methods.

66. The method of claim 60, wherein the activity of the proficient enzyme conjugate is indicated by precipitation of a soluble component and wherein the soluble component is a BSA protein or a pH sensitive polymer selected from the group consisting of methyl acrylic acid, methyl methacrylate, methacrylic acid 2-(dimethylamino) ethyl ester, and N-hydroxymethyl acrylamide.

67. The method of claim 55, further comprising providing one or more inactive pro-enzymes in the detection zone of the lateral flow assay device as substrates.

68. The method of claim 55, wherein the lateral flow assay device further comprises an absorptive pad located downstream of the detection zone.

69. The method of claim 55, wherein the substrate is allyl hexanoate and the proficient enzyme is carboxylesterase.

* * * * *